US008129164B2

(12) United States Patent
Wahl et al.

(10) Patent No.: US 8,129,164 B2
(45) Date of Patent: Mar. 6, 2012

(54) CRYSTALLOGRAPHIC STRUCTURE OF MNK-1 AND MNK-2 PROTEINS

(75) Inventors: Markus Wahl, Gottingen (DE); Ralf Jauch, Jena (DE); Kay Schreiter, Gottingen (DE); Stefan Jakel, Gottingen (DE)

(73) Assignees: Max-Planck-Gesellschaft zur Forderung der Wissenschaften E.V., Munich (DE); Boehringer Ingelheim International GmbH, Rhein (DE)

( * ) Notice: Subject to any disclaimer, the term of this patent is extended or adjusted under 35 U.S.C. 154(b) by 0 days.

(21) Appl. No.: 13/022,765

(22) Filed: Feb. 8, 2011

(65) Prior Publication Data
US 2011/0159568 A1  Jun. 30, 2011

Related U.S. Application Data

(62) Division of application No. 11/908,041, filed as application No. PCT/EP2006/002139 on Mar. 8, 2006, now Pat. No. 7,943,357.

(30) Foreign Application Priority Data

Mar. 8, 2005 (EP) .................................... 05005057
Sep. 13, 2005 (EP) .................................... 05019899

(51) Int. Cl.
*C12N 9/12* (2006.01)
(52) U.S. Cl. ........................................................ 435/194
(58) Field of Classification Search ....................... None
See application file for complete search history.

(56) References Cited

OTHER PUBLICATIONS

J. M. Wiencek New Stratgies for Protein Crystal Growth. Ann. Rev. Biomed. Eng. 1999, 1, 505-434.*
Goldberg, Jonathan, et al., "Structural Basis for the Autoinhibition of Calcium/Calmodulin-dependent protein kinase I", Cell, vol. 84, noo. 6, 1996, pp. 875-887.
Databse PDB Online, Oct. 4, 2005, Jauch et al., "Structure of Human Mnk2 Kinase Domain".
European Search Report.
International Preliminary Report and Written Opinion of the International Searching Authority.

* cited by examiner

*Primary Examiner* — Nashaat Nashed
(74) *Attorney, Agent, or Firm* — Thomas, Kayden, Horstemeyer & Risley, LLP

(57) ABSTRACT

The present invention relates to crystalline Mnk-1 and Mnk-2 kinases and, in particular, to the crystal structure of Mnk-1 and Mnk-2 kinase domain.

4 Claims, 20 Drawing Sheets

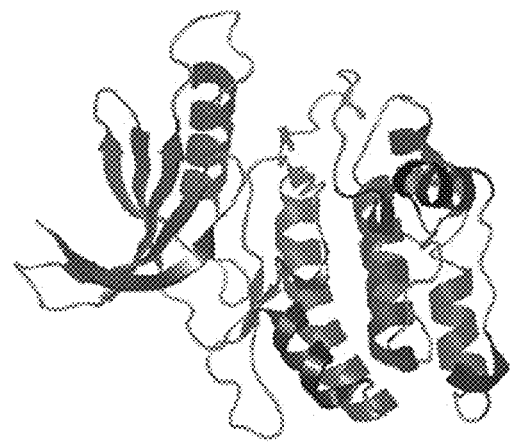

Figure 1A:
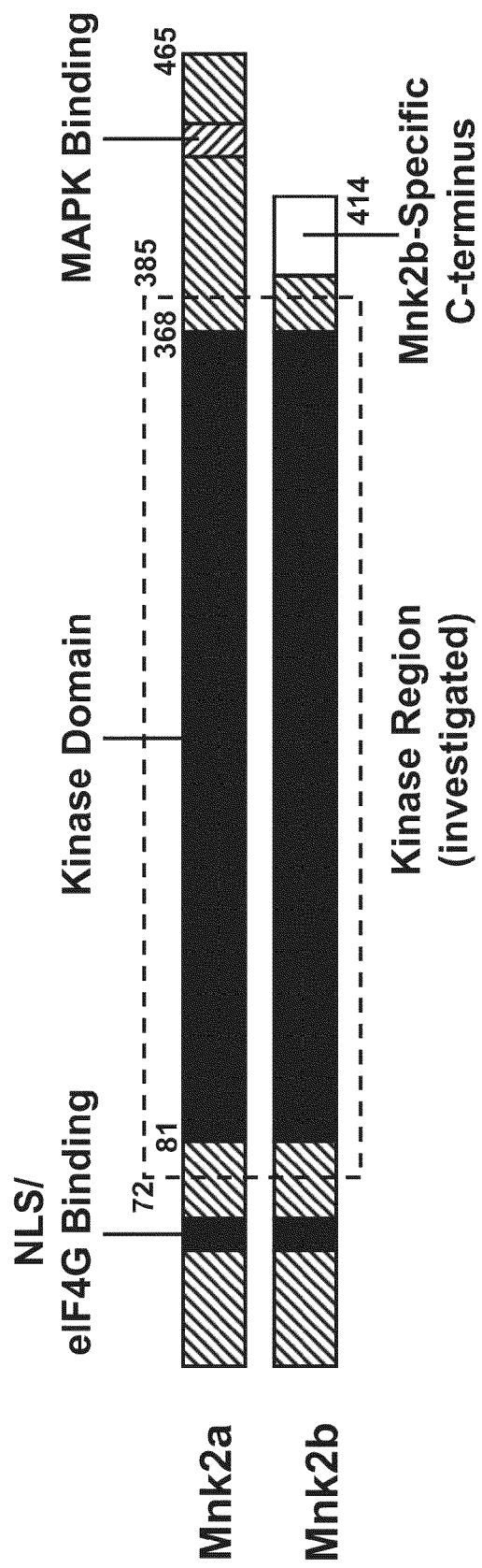

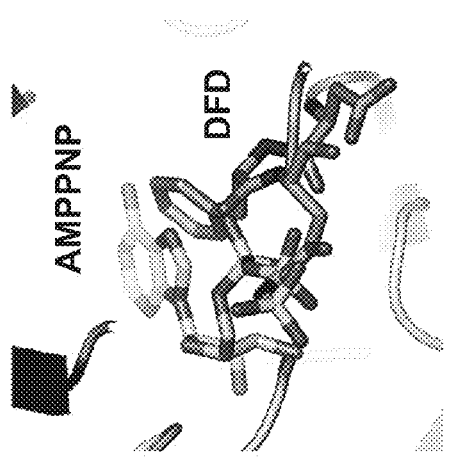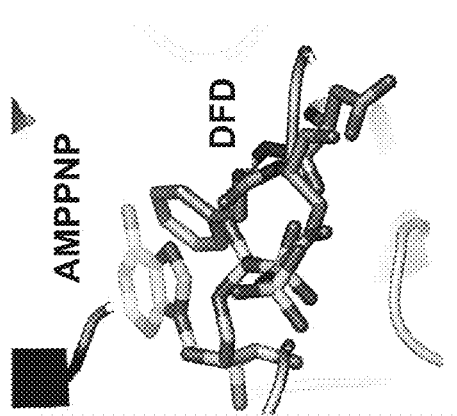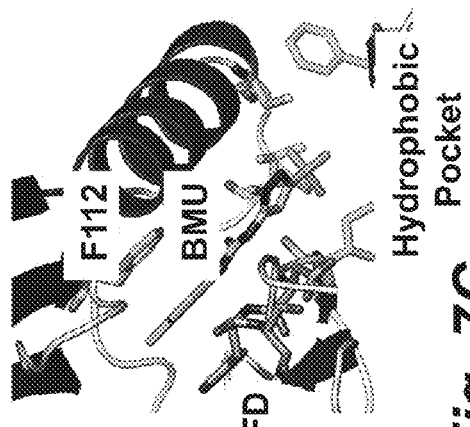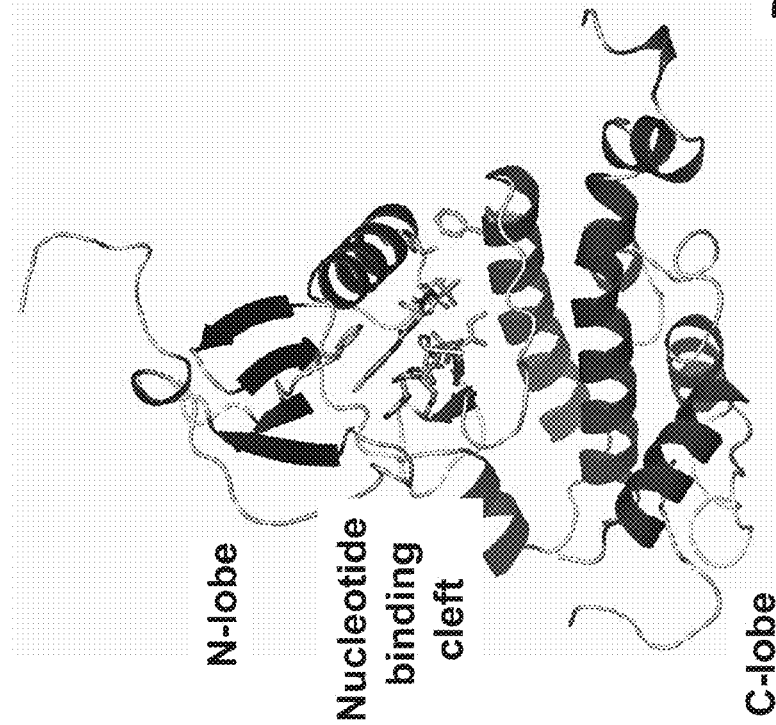
Fig. 7A
Fig. 7B
Fig. 7C

SEQUENCE LISTING

<160> NUMBER OF SEQ ID NOS: 21

<210> SEQ ID NO 1
<211> LENGTH: 29
<212> TYPE: DNA
<213> ORGANISM: Artificial Sequence
<220> FEATURE:
<223> OTHER INFORMATION: Synthetic oligonucleotide forward primer

<400> SEQUENCE: 1
cgggatccac cgacagcttc tcgggcagg                                    29

<210> SEQ ID NO 2
<211> LENGTH: 33
<212> TYPE: DNA
<213> ORGANISM: Artificial Sequence
<220> FEATURE:
<223> OTHER INFORMATION: Synthetic oligonucleotide reverse primer

<400> SEQUENCE: 2
acgcgtcgac ctacctctgc aggaccatgg gag                               33

<210> SEQ ID NO 3
<211> LENGTH: 257
<212> TYPE: PRT
<213> ORGANISM: Homo sapiens

<400> SEQUENCE: 3

Tyr Asp Phe Arg Asp Val Leu Gly Thr Gly Ala Phe Ser Glu Val Ile
1               5                   10                  15

Leu Ala Glu Asp Lys Arg Thr Gln Lys Leu Val Ala Ile Lys Cys Ile
            20                  25                  30

Ala Lys Glu Ala Leu Glu Gly Lys Glu Gly Ser Met Glu Asn Glu Ile
        35                  40                  45

Ala Val Leu His Lys Ile Lys His Pro Asn Ile Val Ala Leu Asp Asp
    50                  55                  60

Ile Tyr Glu Ser Gly Gly His Leu Tyr Leu Ile Met Gln Leu Val Ser
65                  70                  75                  80

Gly Gly Glu Leu Phe Asp Arg Ile Val Glu Lys Gly Phe Tyr Thr Glu
                85                  90                  95

Arg Asp Ala Ser Arg Leu Ile Phe Gln Val Leu Asp Ala Val Lys Tyr
            100                 105                 110

Leu His Asp Leu Gly Ile Val His Arg Asp Leu Lys Pro Glu Asn Leu
        115                 120                 125

Leu Tyr Tyr Ser Leu Asp Glu Asp Ser Lys Ile Met Ile Ser Asp Phe
    130                 135                 140

Gly Leu Ser Lys Met Glu Asp Pro Gly Ser Val Leu Ser Thr Ala Cys
145                 150                 155                 160

Gly Thr Pro Gly Tyr Val Ala Pro Glu Val Leu Ala Gln Lys Pro Tyr
                165                 170                 175

Ser Lys Ala Val Asp Cys Trp Ser Ile Gly Val Ile Ala Tyr Ile Leu
            180                 185                 190

Leu Cys Gly Tyr Pro Pro Phe Tyr Asp Glu Asn Asp Ala Lys Leu Phe
        195                 200                 205

Glu Gln Ile Leu Lys Ala Glu Tyr Glu Phe Asp Ser Pro Tyr Trp Asp
    210                 215                 220

Asp Ile Ser Asp Ser Ala Lys Asp Phe Ile Arg His Leu Met Glu Lys
225                 230                 235                 240

Asp Pro Glu Lys Arg Phe Thr Cys Glu Gln Ala Leu Gln His Pro Trp
                245                 250                 255

Ile

<210> SEQ ID NO 4
<211> LENGTH: 286
<212> TYPE: PRT
<213> ORGANISM: Homo sapiens

<400> SEQUENCE: 4

Tyr Lys Leu Thr Ser Glu Leu Leu Gly Glu Gly Ala Tyr Ala Lys Val
1               5                   10                  15

Gln Gly Ala Val Ser Leu Gln Asn Gly Lys Glu Tyr Ala Val Lys Ile
            20                  25                  30

Ile Glu Lys Gln Ala Gly His Ser Arg Ser Arg Val Phe Arg Glu Val
        35                  40                  45

Glu Thr Leu Tyr Gln Cys Gln Gly Asn Lys Asn Ile Leu Glu Leu Ile
    50                  55                  60

Glu Phe Phe Glu Asp Asp Thr Arg Phe Tyr Leu Val Phe Glu Lys Leu
65                  70                  75                  80

Gln Gly Gly Ser Ile Leu Ala His Ile Gln Lys Gln Lys His Phe Asn
                85                  90                  95

Glu Arg Glu Ala Ser Arg Val Val Arg Asp Val Ala Ala Ala Leu Asp
            100                 105                 110

Phe Leu His Thr Lys Gly Ile Ala His Arg Asp Leu Lys Pro Glu Asn
        115                 120                 125

Ile Leu Cys Glu Ser Pro Glu Lys Val Ser Pro Val Lys Ile Cys Asp
    130                 135                 140

Phe Asp Leu Gly Ser Gly Met Lys Leu Asn Asn Ser Cys Thr Pro Ile
145                 150                 155                 160

Thr Thr Pro Glu Leu Thr Thr Pro Cys Gly Ser Ala Glu Tyr Met Ala
                165                 170                 175

Pro Glu Val Val Glu Val Phe Thr Asp Gln Ala Thr Phe Tyr Asp Lys
            180                 185                 190

Arg Cys Asp Leu Trp Ser Leu Gly Val Val Leu Tyr Ile Met Leu Ser
        195                 200                 205

Gly Tyr Pro Pro Phe Val Gly His Cys Gly Ala Asp Cys Gly Trp Asp
    210                 215                 220

Arg Gly Glu Val Cys Arg Val Cys Gln Asn Lys Leu Phe Glu Ser Ile
225                 230                 235                 240

Gln Glu Gly Lys Tyr Glu Phe Pro Asp Lys Asp Trp Ala His Ile Ser
                245                 250                 255

Ser Glu Ala Lys Asp Leu Ile Ser Lys Leu Leu Val Arg Asp Ala Lys
            260                 265                 270

Gln Arg Leu Ser Ala Ala Gln Val Leu Gln His Pro Trp Val
        275                 280                 285

<210> SEQ ID NO 5
<211> LENGTH: 287
<212> TYPE: PRT
<213> ORGANISM: Drosophila melanogaster

<400> SEQUENCE: 5

Tyr Lys Leu Thr Gly Glu Ile Leu Gly Glu Gly Ala Tyr Ala Ser Val
1               5                   10                  15

Gln Thr Cys Val Asn Ile Tyr Thr Asp Leu Glu Tyr Ala Val Lys Val

```
            20                  25                  30
Ile Asp Lys Ile Pro Gly His Ala Arg Ala Arg Val Phe Arg Glu Val
        35                  40                  45

Glu Thr Phe His His Cys Gln Gly His Leu Gly Ile Leu Gln Leu Ile
    50                  55                  60

Glu Phe Phe Glu Asp Asp Glu Lys Phe Tyr Leu Val Phe Glu Lys Ile
65                  70                  75                  80

Asn Gly Gly Pro Leu Leu Ser Arg Ile Gln Glu His Ile Cys Phe Ser
                85                  90                  95

Glu His Glu Ala Ser Gln Ile Ile Lys Glu Ile Ala Ser Gly Leu Asp
            100                 105                 110

Phe Leu His Lys Lys Gly Ile Ala His Arg Asp Leu Lys Pro Glu Asn
        115                 120                 125

Ile Leu Cys Val Lys Thr Asp Ser Leu Cys Pro Ile Lys Ile Cys Asp
    130                 135                 140

Phe Asp Leu Gly Ser Gly Ile Lys Phe Thr Thr Asp Ile Ser Ser Pro
145                 150                 155                 160

Ala Ala Thr Pro Gln Leu Leu Thr Pro Val Gly Ser Ala Glu Phe Met
                165                 170                 175

Ala Pro Glu Val Val Asp Leu Phe Val Gly Glu Ala His Tyr Tyr Asp
            180                 185                 190

Lys Arg Cys Asp Leu Trp Ser Leu Gly Val Ile Ala Tyr Ile Leu Leu
        195                 200                 205

Cys Gly Tyr Pro Pro Phe Ser Gly Asn Cys Gly Glu Asp Cys Gly Trp
    210                 215                 220

Asn Arg Gly Glu Asn Cys Arg Thr Cys Gln Glu Leu Leu Phe Glu Ser
225                 230                 235                 240

Ile Gln Glu Gly His Phe Ser Phe Pro Glu Ala Glu Trp His Asp Val
                245                 250                 255

Ser Asp Glu Ala Lys Asp Leu Ile Ser Asn Leu Leu Val Lys Lys Ala
            260                 265                 270

Ser Asn Arg Leu Ser Ala Glu Ala Val Leu Asn His Pro Trp Ile
        275                 280                 285

<210> SEQ ID NO 6
<211> LENGTH: 291
<212> TYPE: PRT
<213> ORGANISM: Caenorhabditis elegans

<400> SEQUENCE: 6

Tyr Lys Leu Thr Asp Glu His Leu Gly Ser Gly Ala Tyr Gly Ser Val
1               5                   10                  15

Thr Thr Cys Lys Ser Ile Lys Ser Gly Val Glu Tyr Ala Val Lys Ile
            20                  25                  30

Val Asp Lys Gln Gly Glu Thr His Ser Arg Lys Arg Ile Leu Arg Glu
        35                  40                  45

Val Asn Ile Phe Lys Thr Cys Lys Asp His Pro Asn Ile Val Gln Leu
    50                  55                  60

Leu Asp Trp Phe Glu Asp Glu Thr Asn Phe Tyr Leu Val Met Glu Lys
65                  70                  75                  80

Met Arg Gly Gly Pro Leu Leu Gln His Ile Leu Gln Arg Lys Tyr Phe
                85                  90                  95

Thr Glu Glu Glu Ala Arg Arg Val Thr Lys Asp Ile Ser Leu Ala Leu
            100                 105                 110

Lys Phe Met His Asp Arg Gly Ile Ala His Arg Asp Val Lys Pro Glu
```

```
                115                 120                 125
Asn Val Leu Cys Thr Asp Pro Asn His Val Ser Pro Val Lys Leu Cys
    130                 135                 140

Asp Leu Asp Leu Ala Ser Gln Arg Pro Gln His Glu Arg His Pro
145                 150                 155                 160

Leu Ser Gln Val Ala Ser Glu Pro Asp Leu Ala Ser Pro Val Gly Ser
                165                 170                 175

Ala Glu Phe Met Ala Pro Glu Val Val Asp Ala Tyr Val Gly Asp Ser
                180                 185                 190

Leu Lys Tyr Asp Lys Lys Cys Asp Thr Trp Ser Leu Gly Val Ile Leu
        195                 200                 205

Tyr Ile Met Leu Ala Gly Tyr Ala Pro Phe Gln Gly Met Cys Asp Asp
    210                 215                 220

Glu Asp Cys Gly Trp Ser Glu Gly Lys Pro Cys Glu Asp Cys Gln Gln
225                 230                 235                 240

Asp Leu Phe His Arg Ile Gln Asp Gly Tyr Tyr Glu Phe Pro Glu Glu
                245                 250                 255

Glu Trp Gly Met Ile Ser Glu Glu Ala Lys Asp Leu Val Ser Asn Leu
                260                 265                 270

Leu Lys Arg Asp Pro Val Asp Arg Leu Val Thr Val Ser Phe Val Asn
        275                 280                 285

Pro Phe Ala
    290

<210> SEQ ID NO 7
<211> LENGTH: 262
<212> TYPE: PRT
<213> ORGANISM: Homo sapiens

<400> SEQUENCE: 7

Lys Val Thr Ser Gln Val Leu Gly Leu Gly Ile Asn Gly Lys Val Leu
1               5                   10                  15

Gln Ile Phe Asn Lys Arg Thr Gln Glu Lys Phe Ala Leu Lys Met Leu
            20                  25                  30

Gln Asp Cys Pro Lys Ala Arg Arg Glu Val Glu Leu His Trp Arg Ala
        35                  40                  45

Ser Gln Cys Pro Asp Ile Val Arg Ile Val Asp Val Tyr Glu Asn Leu
    50                  55                  60

Tyr Ala Gly Arg Lys Cys Leu Leu Ile Val Met Glu Cys Leu Asp Gly
65                  70                  75                  80

Gly Glu Leu Phe Ser Arg Ile Gln Asp Arg Gly Asp Gln Ala Phe Thr
                85                  90                  95

Glu Arg Glu Ala Ser Glu Ile Met Lys Ser Ile Gly Glu Ala Ile Gln
            100                 105                 110

Tyr Leu His Ser Ile Asn Ile Ala His Arg Asp Val Lys Pro Glu Asn
        115                 120                 125

Leu Leu Tyr Thr Ser Lys Arg Pro Asn Ala Ile Leu Lys Leu Thr Asp
    130                 135                 140

Phe Gly Phe Ala Lys Glu Thr Thr Ser His Asn Ser Leu Thr Thr Pro
145                 150                 155                 160

Cys Tyr Thr Pro Tyr Tyr Val Ala Pro Glu Val Leu Gly Pro Glu Lys
                165                 170                 175

Tyr Asp Lys Ser Cys Asp Met Leu Val Leu Gly Val Ile Met Tyr Ile
            180                 185                 190

Leu Leu Cys Gly Tyr Pro Pro Phe Tyr Ser Asn His Gly Leu Ala Ile
```

```
            195                 200                 205
Ser Pro Gly Met Lys Thr Arg Ile Arg Met Gly Gln Tyr Glu Phe Pro
    210                 215                 220

Asn Pro Glu Trp Ser Glu Val Ser Glu Val Lys Met Leu Ile Arg
225                 230                 235                 240

Asn Leu Leu Lys Thr Glu Pro Thr Gln Arg Met Thr Ile Thr Glu Phe
                245                 250                 255

Met Asn His Pro Trp Ile
            260

<210> SEQ ID NO 8
<211> LENGTH: 263
<212> TYPE: PRT
<213> ORGANISM: Homo sapiens

<400> SEQUENCE: 8

Tyr Asp Thr Gly Glu Glu Leu Gly Ser Gly Gln Phe Ala Val Val Lys
1               5                   10                  15

Lys Cys Arg Glu Lys Ser Thr Gly Leu Gln Tyr Ala Ala Lys Phe Ile
            20                  25                  30

Lys Lys Arg Arg Thr Lys Ser Ser Arg Arg Gly Val Ser Arg Glu Asp
        35                  40                  45

Ile Glu Arg Glu Val Ser Ile Leu Lys Glu Ile Gln His Pro Asn Val
    50                  55                  60

Ile Thr Leu His Glu Val Tyr Glu Asn Lys Thr Asp Val Ile Leu Ile
65                  70                  75                  80

Leu Glu Leu Val Ala Gly Gly Glu Leu Phe Asp Phe Leu Ala Glu Lys
                85                  90                  95

Glu Ser Leu Thr Glu Glu Ala Thr Glu Phe Leu Lys Gln Ile Leu
            100                 105                 110

Asn Gly Val Tyr Tyr Leu His Ser Leu Gln Ile Ala His Phe Asp Leu
        115                 120                 125

Lys Pro Glu Asn Ile Met Leu Leu Asp Arg Asn Val Pro Lys Pro Arg
    130                 135                 140

Ile Lys Ile Ile Asp Phe Gly Leu Ala His Lys Ile Asp Phe Gly Asn
145                 150                 155                 160

Glu Phe Lys Asn Ile Phe Gly Thr Pro Glu Phe Val Ala Pro Glu Ile
                165                 170                 175

Val Asn Tyr Glu Pro Leu Gly Leu Glu Ala Asp Met Trp Ser Ile Gly
            180                 185                 190

Val Ile Thr Tyr Ile Leu Leu Ser Gly Ala Ser Pro Phe Leu Gly Asp
        195                 200                 205

Thr Lys Gln Glu Thr Leu Ala Asn Val Ser Ala Val Asn Tyr Glu Phe
    210                 215                 220

Glu Asp Glu Tyr Phe Ser Asn Thr Ser Ala Leu Ala Lys Asp Phe Ile
225                 230                 235                 240

Arg Arg Leu Leu Val Lys Asp Pro Lys Lys Arg Met Thr Ile Gln Asp
                245                 250                 255

Ser Leu Gln His Pro Trp Ile
            260

<210> SEQ ID NO 9
<211> LENGTH: 285
<212> TYPE: PRT
<213> ORGANISM: Homo sapiens

<400> SEQUENCE: 9
```

Gln Leu Gln Glu Asp Val Leu Gly Gly Ala His Ala Arg Val Gln
1               5                   10                  15

Thr Cys Ile Asn Leu Ile Thr Ser Gln Glu Tyr Ala Val Lys Ile Ile
            20                  25                  30

Glu Lys Gln Pro Gly His Ile Arg Ser Arg Val Phe Arg Glu Val Glu
                35                  40                  45

Met Leu Tyr Gln Cys Gln Gly His Arg Asn Val Leu Glu Leu Ile Glu
    50                  55                  60

Phe Phe Glu Glu Glu Asp Arg Phe Tyr Leu Val Phe Glu Lys Met Arg
65                  70                  75                  80

Gly Gly Ser Ile Leu Ser His Ile His Lys Arg His Phe Asn Glu
                85                  90                  95

Leu Glu Ala Ser Val Val Val Gln Asp Val Ala Ser Ala Leu Asp Phe
                100                 105                 110

Leu His Asn Lys Gly Ile Ala His Arg Asp Leu Lys Pro Glu Asn Ile
                115                 120                 125

Leu Cys Glu His Pro Asn Gln Val Ser Pro Val Lys Ile Cys Asp Phe
        130                 135                 140

Asp Leu Gly Ser Gly Ile Lys Leu Asn Gly Asp Cys Ser Pro Ile Ser
145                 150                 155                 160

Thr Pro Glu Leu Leu Thr Pro Cys Gly Ser Ala Glu Tyr Met Ala Pro
                165                 170                 175

Glu Val Val Glu Ala Phe Ser Glu Glu Ala Ser Ile Tyr Asp Lys Arg
                180                 185                 190

Cys Asp Leu Trp Ser Leu Gly Val Ile Leu Tyr Ile Leu Leu Ser Gly
        195                 200                 205

Tyr Pro Pro Phe Val Gly Arg Cys Gly Ser Asp Cys Gly Trp Asp Arg
210                 215                 220

Gly Glu Ala Cys Pro Ala Cys Gln Asn Met Leu Phe Glu Ser Ile Gln
225                 230                 235                 240

Glu Gly Lys Tyr Glu Phe Pro Asp Lys Asp Trp Ala His Ile Ser Cys
                245                 250                 255

Ala Ala Lys Asp Leu Ile Ser Lys Leu Leu Val Arg Asp Ala Lys Gln
                260                 265                 270

Arg Leu Ser Ala Ala Gln Val Leu Gln His Pro Trp Val
        275                 280                 285

<210> SEQ ID NO 10
<211> LENGTH: 40
<212> TYPE: DNA
<213> ORGANISM: Artificial Sequence
<220> FEATURE:
<223> OTHER INFORMATION: Synthetic mutagenesis oligonucleotide

<400> SEQUENCE: 10
gaagatctgt gacttcggcc tgggcagcgg catcaaactc                           40

<210> SEQ ID NO 11
<211> LENGTH: 40
<212> TYPE: DNA
<213> ORGANISM: Artificial Sequence
<220> FEATURE:
<223> OTHER INFORMATION: Synthetic mutagenesis oligonucleotide

<400> SEQUENCE: 11
gagtttgatg ccgctgccca ggccgaagtc acagatcttc                           40

```
<210> SEQ ID NO 12
<211> LENGTH: 29
<212> TYPE: DNA
<213> ORGANISM: Artificial Sequence
<220> FEATURE:
<223> OTHER INFORMATION: Synthetic oligonucleotide primer

<400> SEQUENCE: 12
cgggatccac tgactccttg ccaggaaag                                      29

<210> SEQ ID NO 13
<211> LENGTH: 33
<212> TYPE: DNA
<213> ORGANISM: Artificial Sequence
<220> FEATURE:
<223> OTHER INFORMATION: Synthetic oligonucleotide primer

<400> SEQUENCE: 13
acgcgtcgac ctatccctttt tctggagctt gcc                                33

<210> SEQ ID NO 14
<211> LENGTH: 12
<212> TYPE: PRT
<213> ORGANISM: Artificial Sequence
<220> FEATURE:
<223> OTHER INFORMATION: Synthetic inhibitor peptide

<400> SEQUENCE: 14

Ala Pro Glu Val Val Glu Ala Phe Ser Glu Glu Ala
1               5                   10

<210> SEQ ID NO 15
<211> LENGTH: 7
<212> TYPE: PRT
<213> ORGANISM: Artificial Sequence
<220> FEATURE:
<223> OTHER INFORMATION: Synthetic inhibitor peptide

<400> SEQUENCE: 15

Glu Val Val Glu Ala Phe Ser
1               5

<210> SEQ ID NO 16
<211> LENGTH: 12
<212> TYPE: PRT
<213> ORGANISM: Artificial Sequence
<220> FEATURE:
<223> OTHER INFORMATION: Synthetic inhibitor peptide

<400> SEQUENCE: 16

Ala Pro Glu Val Val Glu Val Phe Thr Asp Gln Ala
1               5                   10

<210> SEQ ID NO 17
<211> LENGTH: 7
<212> TYPE: PRT
<213> ORGANISM: Artificial Sequence
<220> FEATURE:
<223> OTHER INFORMATION: Synthetic inhibitor peptide

<400> SEQUENCE: 17

Glu Val Val Glu Val Phe Thr
1               5

<210> SEQ ID NO 18
<211> LENGTH: 424
<212> TYPE: PRT
<213> ORGANISM: Homo sapiens
```

-continued

```
<400> SEQUENCE: 18

Met Val Ser Ser Gln Lys Leu Glu Lys Pro Ile Glu Met Gly Ser Ser
1               5                   10                  15

Glu Pro Leu Pro Ile Ala Asp Gly Asp Arg Arg Lys Lys Lys Arg
            20                  25                  30

Arg Gly Arg Ala Thr Asp Ser Leu Pro Gly Lys Phe Glu Asp Met Tyr
            35                  40                  45

Lys Leu Thr Ser Glu Leu Leu Gly Glu Gly Ala Tyr Ala Lys Val Gln
        50                  55                  60

Gly Ala Val Ser Leu Gln Asn Gly Lys Glu Tyr Ala Val Lys Ile Ile
65                  70                  75                  80

Glu Lys Gln Ala Gly His Ser Arg Ser Arg Val Phe Arg Glu Val Glu
                85                  90                  95

Thr Leu Tyr Gln Cys Gln Gly Asn Lys Asn Ile Leu Glu Leu Ile Glu
            100                 105                 110

Phe Phe Glu Asp Asp Thr Arg Phe Tyr Leu Val Phe Glu Lys Leu Gln
            115                 120                 125

Gly Gly Ser Ile Leu Ala His Ile Gln Lys Gln Lys His Phe Asn Glu
130                 135                 140

Arg Glu Ala Ser Arg Val Val Arg Asp Val Ala Ala Ala Leu Asp Phe
145                 150                 155                 160

Leu His Thr Lys Gly Ile Ala His Arg Asp Leu Lys Pro Glu Asn Ile
                165                 170                 175

Leu Cys Glu Ser Pro Glu Lys Val Ser Pro Val Lys Ile Cys Asp Phe
            180                 185                 190

Asp Leu Gly Ser Gly Met Lys Leu Asn Asn Ser Cys Thr Pro Ile Thr
            195                 200                 205

Thr Pro Glu Leu Thr Thr Pro Cys Gly Ser Ala Glu Tyr Met Ala Pro
        210                 215                 220

Glu Val Val Glu Val Phe Thr Asp Gln Ala Thr Phe Tyr Asp Lys Arg
225                 230                 235                 240

Cys Asp Leu Trp Ser Leu Gly Val Val Leu Tyr Ile Met Leu Ser Gly
                245                 250                 255

Tyr Pro Pro Phe Val Gly His Cys Gly Ala Asp Cys Gly Trp Asp Arg
            260                 265                 270

Gly Glu Val Cys Arg Val Cys Gln Asn Lys Leu Phe Glu Ser Ile Gln
            275                 280                 285

Glu Gly Lys Tyr Glu Phe Pro Asp Lys Asp Trp Ala His Ile Ser Ser
        290                 295                 300

Glu Ala Lys Asp Leu Ile Ser Lys Leu Leu Val Arg Asp Ala Lys Gln
305                 310                 315                 320

Arg Leu Ser Ala Ala Gln Val Leu Gln His Pro Trp Val Gln Gly Gln
                325                 330                 335

Ala Pro Glu Lys Gly Leu Pro Thr Pro Gln Val Leu Gln Arg Asn Ser
            340                 345                 350

Ser Thr Met Asp Leu Thr Leu Phe Ala Ala Glu Ala Ile Ala Leu Asn
            355                 360                 365

Arg Gln Leu Ser Gln His Glu Glu Asn Glu Leu Ala Glu Glu Pro Glu
        370                 375                 380

Ala Leu Ala Asp Gly Leu Cys Ser Met Lys Leu Ser Pro Pro Cys Lys
385                 390                 395                 400

Ser Arg Leu Ala Arg Arg Arg Ala Leu Ala Gln Ala Gly Arg Gly Glu
                405                 410                 415
```

Asp Arg Ser Pro Pro Thr Ala Leu
            420

<210> SEQ ID NO 19
<211> LENGTH: 465
<212> TYPE: PRT
<213> ORGANISM: Homo sapiens

<400> SEQUENCE: 19

Met Val Gln Lys Lys Pro Ala Glu Leu Gln Gly Phe His Arg Ser Phe
1               5                   10                  15

Lys Gly Gln Asn Pro Phe Glu Leu Ala Phe Ser Leu Asp Gln Pro Asp
            20                  25                  30

His Gly Asp Ser Asp Phe Gly Leu Gln Cys Ser Ala Arg Pro Asp Met
        35                  40                  45

Pro Ala Ser Gln Pro Ile Asp Ile Pro Asp Ala Lys Lys Arg Gly Lys
    50                  55                  60

Lys Lys Lys Arg Gly Arg Ala Thr Asp Ser Phe Ser Gly Arg Phe Glu
65                  70                  75                  80

Asp Val Tyr Gln Leu Gln Glu Asp Val Leu Gly Glu Gly Ala His Ala
                85                  90                  95

Arg Val Gln Thr Cys Ile Asn Leu Ile Thr Ser Gln Glu Tyr Ala Val
            100                 105                 110

Lys Ile Ile Glu Lys Gln Pro Gly His Ile Arg Ser Arg Val Phe Arg
        115                 120                 125

Glu Val Glu Met Leu Tyr Gln Cys Gln Gly His Arg Asn Val Leu Glu
    130                 135                 140

Leu Ile Glu Phe Phe Glu Glu Asp Arg Phe Tyr Leu Val Phe Glu
145                 150                 155                 160

Lys Met Arg Gly Gly Ser Ile Leu Ser His Ile His Lys Arg Arg His
                165                 170                 175

Phe Asn Glu Leu Glu Ala Ser Val Val Val Gln Asp Val Ala Ser Ala
            180                 185                 190

Leu Asp Phe Leu His Asn Lys Gly Ile Ala His Arg Asp Leu Lys Pro
        195                 200                 205

Glu Asn Ile Leu Cys Glu His Pro Asn Gln Val Ser Pro Val Lys Ile
    210                 215                 220

Cys Asp Phe Asp Leu Gly Ser Gly Ile Lys Leu Asn Gly Asp Cys Ser
225                 230                 235                 240

Pro Ile Ser Thr Pro Glu Leu Leu Thr Pro Cys Gly Ser Ala Glu Tyr
                245                 250                 255

Met Ala Pro Glu Val Val Glu Ala Phe Ser Glu Glu Ala Ser Ile Tyr
            260                 265                 270

Asp Lys Arg Cys Asp Leu Trp Ser Leu Gly Val Ile Leu Tyr Ile Leu
        275                 280                 285

Leu Ser Gly Tyr Pro Pro Phe Val Gly Arg Cys Gly Ser Asp Cys Gly
    290                 295                 300

Trp Asp Arg Gly Glu Ala Cys Pro Ala Cys Gln Asn Met Leu Phe Glu
305                 310                 315                 320

Ser Ile Gln Glu Gly Lys Tyr Glu Glu Pro Asp Lys Asp Trp Ala His
                325                 330                 335

Ile Ser Cys Ala Ala Lys Asp Leu Ile Ser Lys Leu Leu Val Arg Asp
            340                 345                 350

Ala Lys Gln Arg Leu Ser Ala Ala Gln Val Leu Gln His Pro Trp Val
        355                 360                 365

-continued

```
Gln Gly Cys Ala Pro Glu Asn Thr Leu Pro Thr Pro Met Val Leu Gln
    370                 375                 380

Arg Asn Ser Cys Ala Lys Asp Leu Thr Ser Phe Ala Ala Glu Ala Ile
385                 390                 395                 400

Ala Met Asn Arg Gln Leu Ala Gln His Asp Glu Asp Leu Ala Glu Glu
                405                 410                 415

Glu Ala Ala Gly Gln Gly Gln Pro Val Leu Val Arg Ala Thr Ser Arg
            420                 425                 430

Cys Leu Gln Leu Ser Pro Pro Ser Gln Ser Lys Leu Ala Gln Arg Arg
        435                 440                 445

Gln Arg Ala Ser Leu Ser Ser Ala Pro Val Val Leu Val Gly Asp His
    450                 455                 460

Ala
465

<210> SEQ ID NO 20
<211> LENGTH: 414
<212> TYPE: PRT
<213> ORGANISM: Homo sapiens

<400> SEQUENCE: 20

Met Val Gln Lys Lys Pro Ala Glu Leu Gln Gly Phe His Arg Ser Phe
1               5                   10                  15

Lys Gly Gln Asn Pro Phe Glu Leu Ala Phe Ser Leu Asp Gln Pro Asp
            20                  25                  30

His Gly Asp Ser Asp Phe Gly Leu Gln Cys Ser Ala Arg Pro Asp Met
        35                  40                  45

Pro Ala Ser Gln Pro Ile Asp Ile Pro Asp Ala Lys Lys Arg Gly Lys
    50                  55                  60

Lys Lys Lys Arg Gly Arg Ala Thr Asp Ser Phe Ser Gly Arg Phe Glu
65                  70                  75                  80

Asp Val Tyr Gln Leu Gln Glu Asp Val Leu Gly Glu Gly Ala His Ala
                85                  90                  95

Arg Val Gln Thr Cys Ile Asn Leu Ile Thr Ser Gln Glu Tyr Ala Val
            100                 105                 110

Lys Ile Ile Glu Lys Gln Pro Gly His Ile Arg Ser Arg Val Phe Arg
        115                 120                 125

Glu Val Glu Met Leu Tyr Gln Cys Gln Gly His Arg Asn Val Leu Glu
    130                 135                 140

Leu Ile Glu Phe Phe Glu Glu Asp Arg Phe Tyr Leu Val Phe Glu
145                 150                 155                 160

Lys Met Arg Gly Gly Ser Ile Leu Ser His Ile His Lys Arg Arg His
                165                 170                 175

Phe Asn Glu Leu Glu Ala Ser Val Val Val Gln Asp Val Ala Ser Ala
            180                 185                 190

Leu Asp Phe Leu His Asn Lys Gly Ile Ala His Arg Asp Leu Lys Pro
        195                 200                 205

Glu Asn Ile Leu Cys Glu His Pro Asn Gln Val Ser Pro Val Lys Ile
    210                 215                 220

Cys Asp Phe Asp Leu Gly Ser Gly Ile Lys Leu Asn Gly Asp Cys Ser
225                 230                 235                 240

Pro Ile Ser Thr Pro Glu Leu Leu Thr Pro Cys Gly Ser Ala Glu Tyr
                245                 250                 255

Met Ala Pro Glu Val Val Glu Ala Phe Ser Glu Glu Ala Ser Ile Tyr
            260                 265                 270
```

```
Asp Lys Arg Cys Asp Leu Trp Ser Leu Gly Val Ile Leu Tyr Ile Leu
            275                 280                 285

Leu Ser Gly Tyr Pro Pro Phe Val Gly Arg Cys Gly Ser Asp Cys Gly
        290                 295                 300

Trp Asp Arg Gly Glu Ala Cys Pro Ala Cys Gln Asn Met Leu Phe Glu
305                 310                 315                 320

Ser Ile Gln Glu Gly Lys Tyr Glu Phe Pro Asp Lys Asp Trp Ala His
                325                 330                 335

Ile Ser Cys Ala Ala Lys Asp Leu Ile Ser Lys Leu Leu Val Arg Asp
            340                 345                 350

Ala Lys Gln Arg Leu Ser Ala Ala Gln Val Leu Gln His Pro Trp Val
        355                 360                 365

Gln Gly Cys Ala Pro Glu Asn Thr Leu Pro Thr Pro Met Val Leu Gln
    370                 375                 380

Arg Trp Asp Ser His Phe Leu Leu Pro Pro His Pro Cys Arg Ile His
385                 390                 395                 400

Val Arg Pro Gly Gly Leu Val Arg Thr Val Thr Val Asn Glu
                405                 410

<210> SEQ ID NO 21
<211> LENGTH: 465
<212> TYPE: PRT
<213> ORGANISM: Artificial Sequence
<220> FEATURE:
<223> OTHER INFORMATION: Synthetic polypeptide mutant D228G

<400> SEQUENCE: 21

Met Val Gln Lys Lys Pro Ala Glu Leu Gln Gly Phe His Arg Ser Phe
1               5                   10                  15

Lys Gly Gln Asn Pro Phe Glu Leu Ala Phe Ser Leu Asp Gln Pro Asp
            20                  25                  30

His Gly Asp Ser Asp Phe Gly Leu Gln Cys Ser Ala Arg Pro Asp Met
        35                  40                  45

Pro Ala Ser Gln Pro Ile Asp Ile Pro Asp Ala Lys Lys Arg Gly Lys
    50                  55                  60

Lys Lys Lys Arg Gly Arg Ala Thr Asp Ser Phe Ser Gly Arg Phe Glu
65                  70                  75                  80

Asp Val Tyr Gln Leu Gln Glu Asp Val Leu Gly Glu Gly Ala His Ala
                85                  90                  95

Arg Val Gln Thr Cys Ile Asn Leu Ile Thr Ser Gln Gly Tyr Ala Val
            100                 105                 110

Lys Ile Ile Glu Lys Gln Pro Gly His Ile Arg Ser Arg Val Phe Arg
        115                 120                 125

Glu Val Glu Met Leu Tyr Gln Cys Gln Gly His Arg Asn Val Leu Glu
130                 135                 140

Leu Ile Glu Phe Phe Glu Glu Glu Asp Arg Phe Tyr Leu Val Phe Glu
145                 150                 155                 160

Lys Met Arg Gly Gly Ser Ile Leu Ser His Ile His Lys Arg Arg His
                165                 170                 175

Phe Asn Glu Leu Glu Ala Ser Val Val Val Gln Asp Val Ala Ser Ala
            180                 185                 190

Leu Asp Phe Leu His Asn Lys Gly Ile Ala His Arg Asp Leu Lys Pro
        195                 200                 205

Glu Asn Ile Leu Cys Glu His Pro Asn Gln Val Ser Pro Val Lys Ile
    210                 215                 220
```

-continued

```
Cys Asp Phe Gly Leu Gly Ser Gly Ile Lys Leu Asn Gly Asp Cys Ser
225                 230                 235                 240

Pro Ile Ser Thr Pro Glu Leu Leu Thr Pro Cys Gly Ser Ala Glu Tyr
                245                 250                 255

Met Ala Pro Glu Val Val Glu Ala Phe Ser Glu Glu Ala Ser Ile Tyr
            260                 265                 270

Asp Lys Arg Cys Asp Leu Trp Ser Leu Gly Val Ile Leu Tyr Ile Leu
        275                 280                 285

Leu Ser Gly Tyr Pro Pro Phe Val Gly Arg Cys Gly Ser Asp Cys Gly
    290                 295                 300

Trp Asp Arg Gly Glu Ala Cys Pro Ala Cys Gln Asn Met Leu Phe Glu
305                 310                 315                 320

Ser Ile Gln Glu Gly Lys Tyr Glu Glu Pro Asp Lys Asp Trp Ala His
                325                 330                 335

Ile Ser Cys Ala Ala Lys Asp Leu Ile Ser Lys Leu Leu Val Arg Asp
            340                 345                 350

Ala Lys Gln Arg Leu Ser Ala Ala Gln Val Leu Gln His Pro Trp Val
        355                 360                 365

Gln Gly Cys Ala Pro Glu Asn Thr Leu Pro Thr Pro Met Val Leu Gln
    370                 375                 380

Arg Asn Ser Cys Ala Lys Asp Leu Thr Ser Phe Ala Ala Glu Ala Ile
385                 390                 395                 400

Ala Met Asn Arg Gln Leu Ala Gln His Asp Glu Asp Leu Ala Glu Glu
                405                 410                 415

Glu Ala Ala Gly Gln Gly Gln Pro Val Leu Val Arg Ala Thr Ser Arg
            420                 425                 430

Cys Leu Gln Leu Ser Pro Pro Ser Gln Ser Lys Leu Ala Gln Arg Arg
        435                 440                 445

Gln Arg Ala Ser Leu Ser Ser Ala Pro Val Val Leu Val Gly Asp His
    450                 455                 460

Ala
465
```

CRYSTALLOGRAPHIC STRUCTURE OF MNK-1 AND MNK-2 PROTEINS

This application is a Divisional of U.S. patent application Ser. No. 11/908,041 entitled "Crystallographic structure of Mnk-1 and Mnk-2 proteins", filed on Sep. 7, 2007 and assigned U.S. Pat. No. 7,943,357, which claimed the benefit of PCT/EP2006/002139, international filing date of 8 Mar. 2006.

DESCRIPTION

The present invention relates to crystalline Mnk-1 and Mnk-2 proteins and, in particular, to the crystal structure of the Mnk-1 and Mnk-2 kinase domains.

In humans, more than 500 kinases are known which mediate the transfer of phosphate groups from nucleotides to protein substrates. A detailed understanding of substrate recognition, regulation and catalysis by protein kinases is fundamental to draw a complete picture of highly diverse biological pathways, many of which have direct links to widespread diseases. The crystal structure of the cAMP-dependent protein kinase has provided a first high-resolution picture of the molecular architecture of protein kinases (Knighton et al., Science 253 (5018) (1991) 407-414).

Crystal structures of different human protein kinases provide valuable insights into catalytic and regulatory mechanism and aid the design of specific inhibitors.

Therefore, the subject matter of the present invention is crystalline human Mnk-2 protein and crystalline human Mnk-1 protein, methods of manufacture and applications thereof.

In a first embodiment, the present invention relates to human serine-threonine kinase mitogen-activated kinase (MAP) interacting kinase-2, which is also referred to as Mnk-2 protein. Four Mnk proteins are found in humans, namely two isoforms Mnk-1 and Mnk-2, whereby the latter exists as two splice variants Mnk-2a and Mnk-2b. A splice variant Mnk-1b has also been described. The kinase domains of Mnk-2a and Mnk-2b are identical. It has been demonstrated that Mnk proteins can be activated by members of the MAP kinase family. Specifically, the stress-induced p38 kinases and the mitogen-activated Erk1/2 proteins can fulfill this function. Mnk-1 and Mnk-2 are activated through a similar pathway and exhibit similar substrate specificities. Their amino acid sequence within the kinase domain is largely similar and the below-mentioned amino acids are identical. Mnk kinases may, thus, constitute a convergence point of these two MAP kinase pathways.

Mnk proteins are a subfamily of the MAP kinases-activated protein kinase (MAPKAPK) family of protein kinases which, in turn, belong to the Ca/calmodulin-modulated kinase (CAMK) group.

Mnk's are activated through phosphorylation by two of the three MAPK cascades: the growth factor stimulated Ras-extracellular signal regulated protein kinases (ERK)1/2 and the stress induced p38-pathway (Fukunaga et al., Embo J. (16) (1997) 1921-1933; Embo J. (16) (1997) 1909-1910). The two mammalian Mnk isoforms, Mnk-1 and Mnk-2, phosphorylate the eukaryotic initiation factor 4E (eIF4E) in vitro and in vivo (Scheper et al., Eur J. Biochem. (269) (2001) 5350-5359; Ueda et al., Mol. Cell. Biol. (24) (2004) 6539-6549; Waskiewicz et al., Mol. Cell. Biol. (19) (1999) 1871-1880). eIF4E is an essential component of the translation initiation complex and binds the CAP structures of eukaryotic messenger RNA's (Marcotrigiano et al., Cell (89) (1997) 951-961). Mnk mediated eIF4E phosphorylation appears to stimulate the translation of specific mRNA, e.g. of RFLAT-1 or viral transcripts (Nikolcheva et al., Clin. Invest. (110) (2002) 119-126; Walsh et al., Genet. Dev. 18 (2004) 660-672). In addition, Mnk1 diminishes the translation of the tumor necrosis factor alpha (TNF-$\alpha$) by phosphorylation of hnRNPA1 and may thus play a role in inflammatory diseases (Buxade, 2005, Immunity 23, 177-189). The involvement of Mnk's in lipid metabolism, inflammation and viral translation defines them as a target for pharmaceutical intervention.

Sequence alignment with other members of CAMK group revealed several unique features of Mnk proteins. To reveal the consequences of this observation in structural and functional terms, a crystallographic study on Mnk-2 was performed. According to the invention, a 2.1 Å crystal structure of the kinase domain of Mnk-2 was obtained. The results show that the Apo enzyme of Mnk-2 exhibits an unusual open conformation of a segment corresponding to subdomain XIII of the Hanks scheme including the C terminus of the activation loop and the P+1 loop (Hanks et al., Methods Enzymol. 200 (1991) 38-62). The P+1 loop is known to be important for substrate binding.

The equivalent of the magnesium binding DFG motif, which is conserved as DFD in Mnk proteins, protudes into the ATP binding pocket and obstructs nucleotide binding. Thus, the conserved DF (G/D) at the beginning of the activation loop adopts a conformation which inhibits ATP binding (referred to as DF(G/D) OUT conformation). This reveals an inhibitory mechanism regulating nucleotide binding in contrast to other kinases of known structure of the CAMK group, where the ATP binding cleft is accessible in the non-phosphorylated apo enzyme (DF (G/D) IN conformation). This is the first observation of a DF (G/D) OUT conformation in a Ser/Thr-kinase apo enzyme.

Additionally, a zinc coordinating motif in the C-loop, which has not been described in protein kinases before, was discovered. The Mnk-2 kinase domain contains an insertion of 15 residues in the C-loop which is conserved in length and sequence in Mnk proteins but which is lacking in other kinases. Four conserved cysteines in this insertion serve as zinc ion binding site, as revealed by Mnk-2 structure presented herein. This zinc finger structure marks a docking site for interaction partners.

The present Mnk-2 structure, thus, reveals novel aspects of kinase architecture and regulation which can be used for rational inhibitor design.

Especially preferably, the present invention relates to crystalline human Mnk-2a or Mnk-2b proteins. Mnk-2a is a human protein kinase which targets the translational machinery via phosphorylation of the eukaryotic initiation factor 4e (eIF4E).

Residues known to be involved in the trans-phosphorylation reaction are conserved within the CAMK kinase group (Taylor et al., Structure 2(5) (1994) 345-355; Hanks et al., Science 241(4861) (1988) 42-52). These residues are (A) Lys113;

(B) the catalytic loop (residues 205-210) containing the putative acceptor base Asp205, and (C) the first Asp226 of DF (G/D) motif which coordinates a magnesium ion required for the activation of $\gamma$ phosphate.

However, there are several features distinguishing Mnk proteins from other protein kinases, namely a conserved glycin in the DFG motif N terminal of the activation loop is replaced by an aspartate in all Mnk proteins, resulting in a DFD motif (also referred to as DF (G/D)). This single amino acid substitution cannot be found in any other member of CAMK group. Further, Mnk proteins contain amino acid insertions at three different locations which are all conserved in length. The first insertion (I1) of around 10 amino acids is located at the N terminus of the activation segment following the DFD motif. The second insertion (I2) is upstream of helix F and contains approximately five amino acids. Insertion 3 (I3) is a stretch of 15 amino acids which exhibits a highly conserved pattern within the Mnk subfamily and is located at the N terminus of the loop connecting the G and the H helices of the C lobe. A cluster of four cysteines is present within I3 which is invariable in all Mnks.

In one embodiment, the crystalline human Mnk-2 protein, especially the crystalline Mnk-2a protein (SEQ ID NO.: 19), according to the invention is the complete protein. In other embodiments, which are also preferred, it is not the full-length protein but a truncated form, in particular, a truncated form which comprises at least amino acid residues 72-385 of the sequence according to SEQ ID NO.: 19), which contain the kinase domain (KD). The numbering refers to entries AAG 26337 (Mnk-2b) and AAG 26336 (Mnk-2a). Especially preferably, crystals which allow X-ray structure analysis having a resolution of better than 20 Å, in particular, better than 10 Å and, most preferably, better than 3 Å are concerned.

The crystalline preparations according to the invention preferably have a space group $P3_221$ and unit cell dimensions of a=104.5 Å±3 Å, b=104.5 Å±3 Å and c=72.35 Å±3 Å. According to the invention, crystals diffracting to 2 Å can be produced, whereby its structure was solved by molecular replacement and could be refined to a R factor of 0.21 ($R_{free}$=0.25). Particularly preferably, crystals of human Mnk-2 protein in inactive form are concerned according to the invention.

Further, preferably, the non-phosphorylated Apo form of the Mnk-2 catalytic domain is concerned.

As has been found according to the invention, the activation segment and its C terminal prolongation up to helix αF (αF: residues 270-290) is in an unusual open conformation (The numbering of Mnk-2 amino acid residues corresponds to the nomenclature of EntrezEntry AAG26336). This region corresponds to subdomain XIII in the Hanks classification. The activation segment bears residues which are phosphorylation targets of activating kinases and has been defined as the region being located between two conserved motifs, DF (G/D) and APE, which are 19-32 residues apart.

In striking contrast to known published kinase structures, subdomain XIII of human Mnk-2 protein protrudes from the kinase core. Subdomain XIII includes the P+1 loop which is located between the phosphorylation site Thr249 and the APE motif. The P+1 loop positions the peptide substrate for catalysis.

The protrusion of subdomain XIII points toward topological rearrangements in Mnk proteins which influence substrate recognition, substrate positioning and the activatory mechanism.

Further residues which are involved in ATP hydrolysis and phosphate transfer are largely invariable in protein kinases. Regions involved in catalytic activity include Lys113, Glu129, Asp205 and Asn210 of the amino acid sequence according to SEQ ID NO.: 19. As could be determined from the structural data obtained according to the invention, the crystalline human Mnk-2 protein structure is not accessible to ATP or related compound. Accordingly, the crystals according to the invention preferably are crystals of human Mnk-2 protein in inactive form. A DF (G/D) OUT conformation p38 comparable to the present DF (G/D) OUT conformation in Mak kinases has been shown to be induced through certain chemicals (Pargellis et al., nature structural biology, vol. 9, no. 4 (2002) 268-272). The DF (G/D) OUT conformation provides a novel allosteric binding site with widespread pharmacological applications including the use of alternative substance classes such as diaryl urea inhibitors, in addition to compounds targeting the ATP binding cleft. Further, stabilization of the DF (G/D) OUT conformation will inhibit the enzyme.

Thus, the data presented herein show that the DFD motif of Mnk-2a can assume a conformation which is incompatible with productive ATP binding, i.e. binding of ATP as required for the phosphorylation of substrates. Hence it follows that non-phosphorylated Mnk-2 could not bind ATP or a conformational change in the DFD motif would have to occur first in order to enable ATP binding. The determined conformation of Mnk-2 differs from all other kinases due to the specific sequence of said protein (DFD motif instead of a DFG motif). This information allows to identify inhibitors of Mnk-2 as well as of isoforms and other protein kinases which recognize and stabilize the unproductive DFD conformation. Further, it is possible to provide inhibitors which are specific for Mnk-2 and the kinase domain of Mnk-2, respectively, and do not recognize other kinases. This is possible because other kinases exhibiting the DFG motif have a different sequence.

Thus, inter alia, an ATP binding pocket (herein also referred to as DFD-out-pocket) as well as another pocket (herein also referred to as DFD-in-pocket) could be determined by the structural data according to the invention. In the active conformation the ATP pocket provides a binding site for ATP. Said pocket, is defined, in particular, by amino acid residues Glu129 and Asp205 as well as, further, by amino acid residues Lys113 and Asn210 of the amino acid sequence according to SEQ ID NO.: 19. The second pocket which could be recognized is of particular interest according to the invention. Said second pocket, or DFD-in-pocket, is the site, wherein the Phe of the DFD motif is located in the active structure. In the inactive conformation, the ATP pocket is at least partially occupied by the DFD motif, in particular, by the Phe of the DFD motif. This inactive conformation can be locked by occupying the DFD-in-pocket, in particular, by occupying the DFD-in-pocket by the activation segment or by another molecule, in particular, a small molecule which acts as an inhibitor. By occupying the DFD-in-pocket, an inhibition of the kinase activity is effected, since the ATP cannot access the ATP pocket which is occupied at least partially by the DFD motif in this configuration. The DFD-in-pocket is defined, in particular, by amino acid residues Leu133, His203, Ile142, Leu196 and Ile224 of the amino acid sequence according to SEQ ID NO.: 19. By blocking said DFD in-pocket the inactive structure is locked. It is therefore a subject matter of the present invention to provide molecules which are capable of occupying said pocket and, thus, represent selective inhibitors of Mnk. Thus, inhibitors capable of binding into said DFD-in-pocket represent another subject matter of the invention. Since, in Mnk's, the activation segment, in particular, the insert I2 of the activation segment and, more particularly, the amino acid residue Phe265 of the amino acid sequence according to SEQ ID NO.: 19, blocks the DFD-in-pocket, suitable inhibitors are e.g. small peptides having at least partially the sequence of the activation segment. The activation segment comprises amino acids Asp226 to Cys275 of the amino acid sequence according to SEQ ID NO.: 19 and, in particular, includes the insertion I2 extending from amino acids 263 to 267 of the amino acid sequence according to SEQ ID NO.: 19. Suitable peptidic inhibitors of Mnk, therefore, are peptides having the sequence of the active segment or a contiguous fragment thereof having at least four, more particularly, at least five, preferably at least six, and more preferably, at least eight amino acids thereof. Examples of such inhibitors are (258)APEVVEAFSEEA(269) (SEQ ID NO.:14) or (260)EVVEAFS(266) (SEQ ID NO.:15).

The possibility of providing inhibitors against an allosteric binding site offered by the invention, further, yields inhibitors having markedly improved selectivity. Standard kinase inhibitors against the ATP binding site of kinases have a large cross-reactivity potential due to the high mutual homology of kinases. Thus, inhibitors directed against the ATP binding site normally only have little selectivity, which strongly impedes and limits the development of selective inhibitors. According to the invention, however, it is now possible to provide selective inhibitors binding at an allosteric binding site of Mnk.

One inhibitor which can be used according to the invention is BIRB 796 (Pargellis et al., nature structural biology, vol. 9, no. 4 (2002), 268-272). Another inhibitor is the diaryl urea-based inhibitor (1-(5-tert-butyl-2-methyl-2H-pyrazole-3-yl)-3-(4-chloro-phenyl)-urea.

Further, Mnk proteins contain an insertion between αF and αG which contains an invariant cluster of four cysteines which distinguish Mnk proteins (SEQ ID NOs.: 4 and 9) from other kinases of the CAMK group (SEQ ID NOs.: 3, 5, 6, 7, and 8). These four cysteines cluster in a flexible loop of the molecule, which form a zinc binding site. Thus, this insertion marks a zinc finger-like structure, a unique fingerprint of protein kinases. Further, four conserved glycines are present in this insertion (Gly297, Gly300, Gly304 and Gly308 of the amino acid sequence according to SEQ ID NO.: 19) which provide a torsional flexibility to this region necessary to fold into this hairpin-like module. Zinc finger modules are known to be versatile nucleic acid or protein-binding modules (Krishna et al., Nucleic Acids Res. 31(2) (2003) 532-550). This domain is an adapter module for other proteins, in particular, substrates or regulators.

The crystalline human Mnk-2 kinase according to the invention also comprises mutants, preferably proteins, wherein at least one amino acid, in particular, at least two amino acids of native Mnk-2 kinase have been replaced by another amino acid. Such crystals of mutants can be used advantageously, in particular, for mechanistical studies as well as for studying the binding pockets and for studying interactions with ligands, substrates or inhibitors. To this end, suitably, individual amino acids are selectively exchanged which are located at positions, where an interaction or an influence on the binding capacity is assumed or expected. For this purpose, crystalline human Mnk-2 kinases can be favorable which have, for example, up to 20, more preferably up to 10, even more preferably up to 5 and most preferably maximally 1 mutation. The crystalline human Mnk-2 kinase mutant D228G (SEQ ID NO.: 21) is especially preferred. In a further preferred embodiment, the crystalline human Mnk-2 kinase mutant D228G (SEQ ID NO.: 21) in complex with a ligand, substrate and/or inhibitor, in particular, in complex with the inhibitor staurosporine is concerned.

Preferred mutants have an amino acid exchange at positions Asp226, Phe227 or Asp228 of the amino acid sequence according to SEQ ID NO.: 19.

The invention further relates to a crystalline human Mnk-2 protein (SEQ ID NO.: 19) having a three-dimensional structure defined by all or a selected portion of the structural coordinates shown in Table 1. The coordinates shown in Table 1 were obtained as described in the Examples herein.

In one embodiment, the invention further provides a crystal structure of a human Mnk-2-D228G mutant of the amino acid sequence according to SEQ ID NO.: 21 co-crystallized with the generic protein kinase inhibitor staurosporine. In this structure, the DFG motif flips into the DFG/D-IN conformation allowing staurosporine to bind at its generic binding site within the ATP binding pocket. The coordinates are shown in Table 4. Further provided is a crystal structure of human Mnk-2 kinase D228G mutant of the amino acid sequence according to SEQ ID NO.: 21 without any inhibitor, in particular, without the inhibitor staurosporine. The coordinates thereof are shown in Table 2.

The crystalline human Mnk-2 protein preparations according to the invention, for example, can be prepared by
    i expression of human Mnk-2 protein in cells, e.g. in *E. coli*,
    ii lysing the cells to recover a crude Mnk-2 protein preparation,
    iii purifying the crude Mnk-2 protein preparation, e.g. by affinity tag chromatography, and
    iv crystallizing the purified human Mnk-2 protein, e.g. by vapor diffusion.

The crystalline preparation of human Mnk-2 protein, in particular, human Mnk-2a protein or Mnk-2b protein, and, more preferably, of the kinase domain of human Mnk-2a protein according to the invention, in particular, can be used for the generation of crystal structure data of human Mnk protein. In particular, binding sites or interaction sites with ligands, especially inhibitors or substrates, can be obtained thereby. Further, it is possible to identify binding sites to maintain the proteins in active or inactive form. In particular, the results presented herein for Mnk-2 protein also allow for identification of ligands, especially inhibitors or substrates of isoforms of Mnk-2 such as Mnk-1.

The crystalline preparations according to the invention, preferably, are single crystals and, more preferably, crystals having an edge length of at least 1 µm, more preferably, at least 10 µm and, most preferably, at least 50 µm. The crystals preferably are arranged in such a manner that X-ray structure analysis can be carried out. Therefore, another subject matter of the invention is a crystal structure of human Mnk-2 protein, in particular, human Mnk-2a protein defined by all or a selected portion of the structural coordinates shown in Table 1, 2, or 4. Preferably, the crystal structure of an inactive human Mnk-2a protein is concerned. The crystal structure preferably has a resolution of better than 50 Å, more preferably better than 10 Å and most preferably better than 3 Å.

Using the crystalline human Mnk-2 protein and the crystal structure, respectively, Mnk-2 protein ligands can be designed, identified or prepared. Moreover, it is possible to identify regulatory mechanisms for protein kinases, in particular, also of isoforms of Mnk-2, as described above. For identifying ligands or regulatory mechanisms, in particular, computer-aided modelling programs are used.

Suitable ligands, for example, can be identified by forming molecules having a three-dimensional structure which is complementary to an interaction site of human Mnk-2 protein. Especially preferably, ligands interact with at least one of amino acids Asp 226, Phe 227 and Asp 228 of the amino acid sequence according to SEQ ID NO.: 19. Further preferred ligands interact with at least one amino acid, of which at least one atom is within a predetermined distance to any atom of the DFD motif, preferably within a distance of 7 Å, more preferably 6 Å and, in particular, 5 Å.

Additionally to the computer-assisted screening for identifying ligands a method as described in WO 03/037362 is preferably applied to actually identify and verify ligands.

The structural coordinates of the crystal structure of human Mnk-2 protein given in Table 1, 2, or 4 also can be used to form a three-dimensional representation of the crystal structure of human Mnk-2 protein. The interaction pockets formed in said three-dimensional structure then can be used to identify corresponding ligands by means of their three-dimensional structure.

The structural coordinates provided by the invention which are shown in Table 1, 2, or 4 further can be used to determine the crystal structure of other proteins, whereby the structural coordinates are used for molecular replacement.

The data provided herein are preferably stored on a computer-readable storage medium and provided accordingly.

The invention further relates to ligands, in particular, substrates or inhibitors of Mnk-2 protein of isoforms thereof as well as of other protein kinases obtained by using the crystalline preparations or crystal structures. Such ligands preferably are active agents in pharmaceutical compositions. Said pharmaceutical compositions, in particular, can be used for treating diseases, in the case of which manipulation or, especially inhibition of Mnk-2 proteins is desirable such as, for example, metabolic disorders such as obesity, diabetes and the metabolic syndrome as well as cancer.

In a further embodiment, the present invention relates to crystalline human Mnk-1 protein.

The crystal structure of the Mnk-1 kinase region (Mnk-1-KR) (SEQ ID NO.: 18) adopts a conformation different from the Mnk-2-KR (SEQ ID NO.: 19) although the amino acid sequence of the catalytic domain is 78% identical. The combination of the structural data on Mnk-1 and Mnk-2 enables to draw a dynamic picture of mechanistic events accompanying the activation of Mnk subfamily members.

Also in this embodiment, mutants of human Mnk-1 protein are included, in particular, mutants having at least one amino acid, in particular, at least two amino acids exchanged. As explained above, such mutants can be used, in particular, for mechanistical studies. Preferably, the mutants have ≦20, more preferably ≦10, even more preferably ≦5 and most preferably maximally 1 amino acid exchanged. Preferred sites for amino acid exchange in the case of Mnk-1 are positions Arg90 or Arg93 as well as Arg191, Phe192 or Arg 193.

The invention further relates to a model of Mnk activation in which the N-terminal lobe, the Magnesium binding loop and the activation segment undergo drastic structural rearrangements and proceed sequentially from an autoinhibited to a fully active state. A further aspect of the invention, therefore, is the use of Mnk's to achieve autoinhibition by activation segment mediated repositioning of functional elements.

In its canonical conformation seen in many other protein kinases the C-terminal part of the activation segment folds back and the short helix α-EF and the substrate binding P+1 loop become buried within kinase core in an environment provided by the helixes αF, αG and the catalytic loop (Knighton et al., Science (253) (1991) 414-420; Nolen, Mol. Cell. (15) (2004) 661-675).

Figures 9A, 9B, 9C:
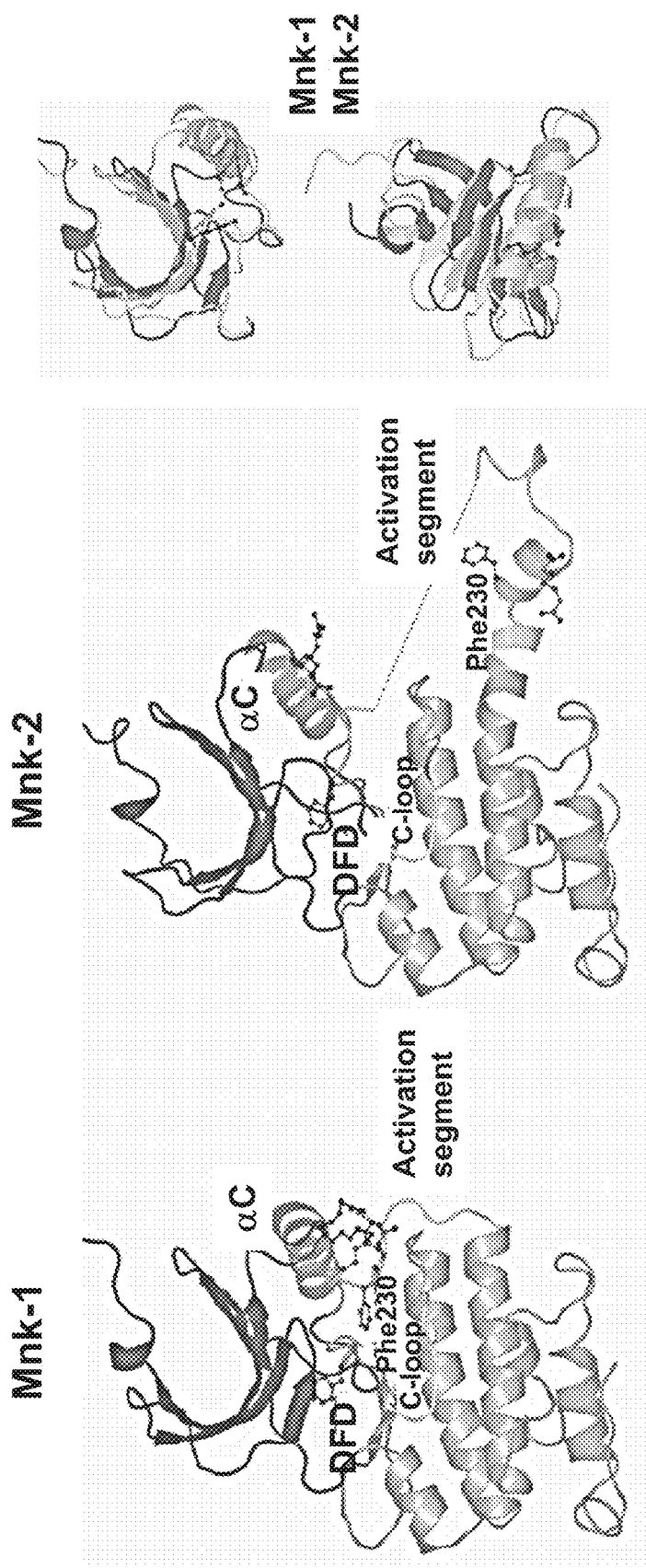

In Mnk-1-KR, however, α-EF unwinds and collapses into the peptide binding groove and thereby alters the configuration of the N terminal lobe and active site residues (FIG. 9A). In particular, the interaction with the αC helix (Arg90:Glu225; Arg93:Glu228 of the amino acid sequence according to SEQ ID NO.: 18) provides a pulling force and displaces αC and the remainder of the N-lobe which leads to lobe closure (FIG. 9A). Residues corresponding to the interacting residues Arg90 and Arg93 of the amino acid sequence according to SEQ ID NO.: 18 are known to bind to phosphate moieties in active state protein kinases (Krupa et al., Mol. Biol. (339) (2004) 1025-1139). Hence, the reconstructed activation segment is predestinated to serve as molecular switch which alters the configuration of the active site. The numbering corresponds to O'Loghlen, A., Gonzalez, V. M., Pineiro, D., Perez-Morgado, M. I., Salinas, M., and Martin, M. E. (2004). Identification and molecular characterization of Mnk1b, a splice variant of human MAP kinase-interacting kinase Mnk1. Exp Cell Res 299, 343-355.

A further effect of this 'wedged' conformation of the activation segment is the exposure of the activation loop which may promote the accessibility of the phosphorylation sites. The lobe closure can be reverted if the interaction between the activation segment and the regulatory C-helix is ceased as demonstrated by the Mnk-2 structure (SEQ ID NO.: 19) (FIG. 9B). In Mnk-2 the activation segment adopts a completely different conformation since it protrudes from the body of the molecule. Consequently, the activation segment: C-helix interaction is relieved and the N-lobe snaps back (FIG. 9B).

When compared with Mnk-1 the N-lobe of Mnk-2 is tilted by approximately 10° leading to an opening of the ATP binding mouth of the kinase (FIG. 9C).

Figure 8A:
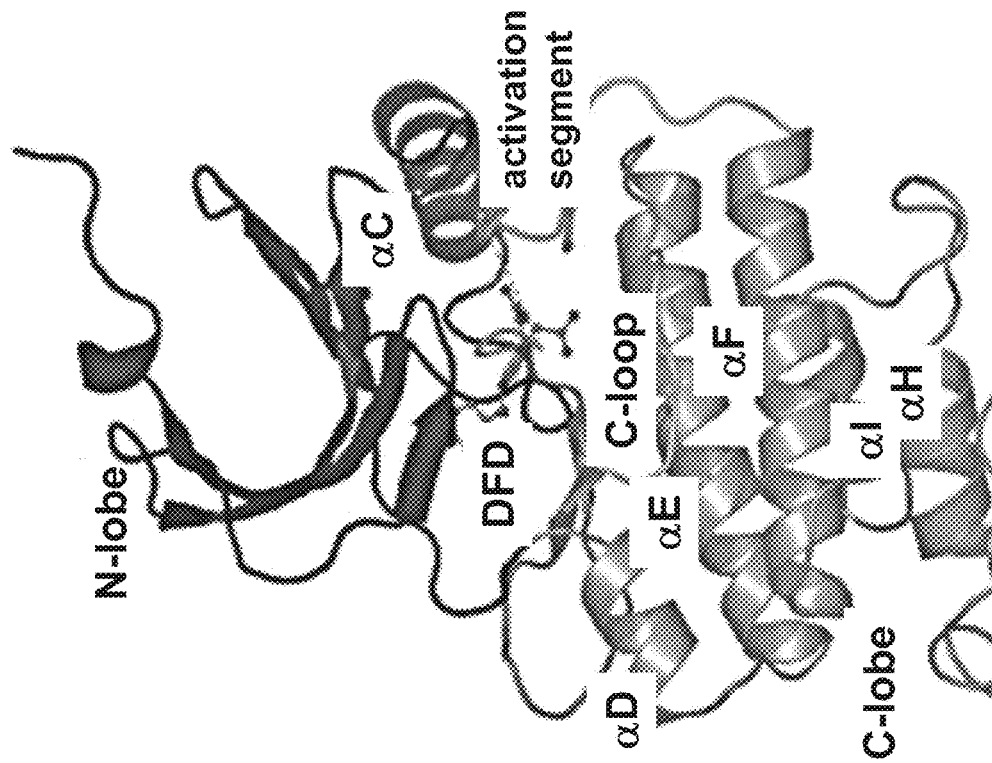
Figure 8A:
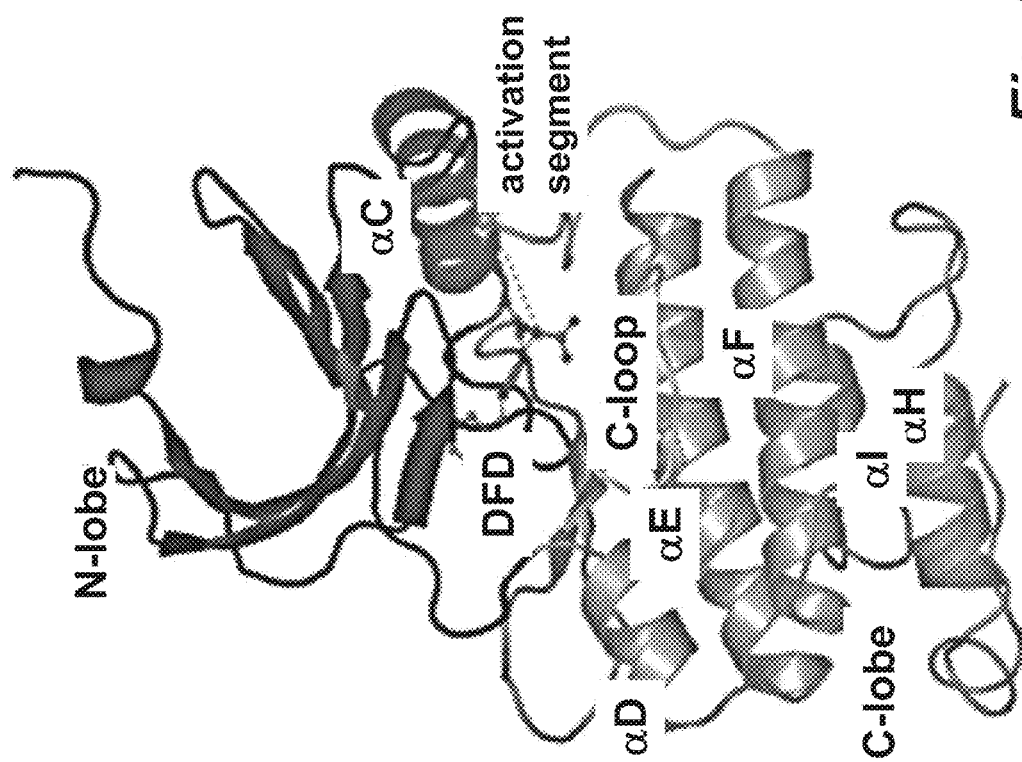
Figure 8B:
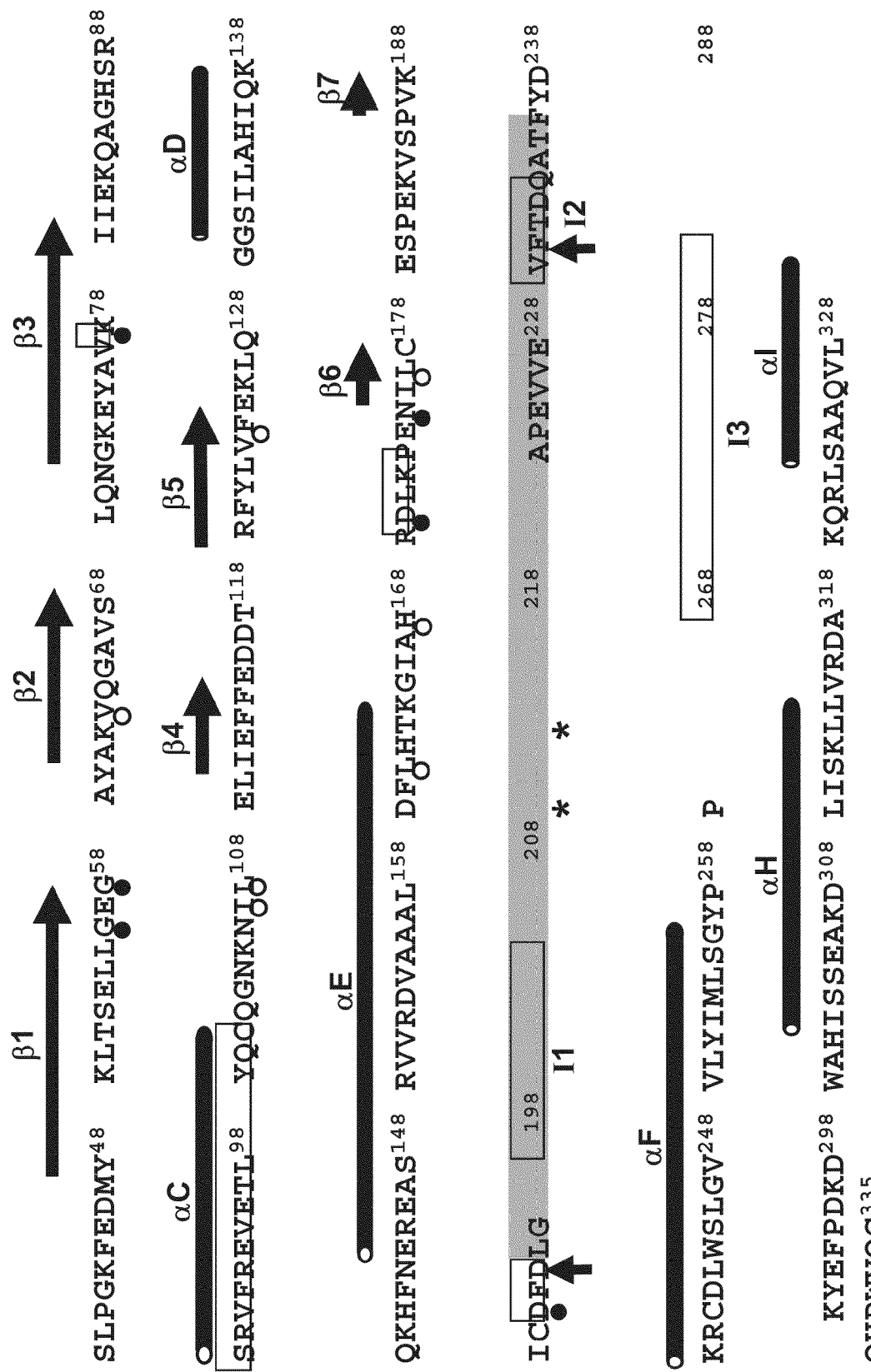

The prolonged and reconstructed activation segment of Mnk-1 bears two amino acid insertions which are not present in most other CAMK group members. Insertion 12 contains Phe-230 of the amino acid sequence according to SEQ ID NO.: 18, a residue which is specific for but conserved within the Mnk subfamily (FIGS. 8A and 8B).

As a result of the novel positioning of the activation segment at the interlobal groove Phe230 comes to lie in the structurally conserved pocket provided by Leu98 and Thr97 emanating from αC, His168 upstream of the C-loop, Ile107, Ile189 and Leu161 (The numbering of Mnk-1 amino acid residues of the amino acid sequence according to SEQ ID NO.: 18 corresponds to the nomenclature of Entrez Entry CAI14764).

Figure 10A:
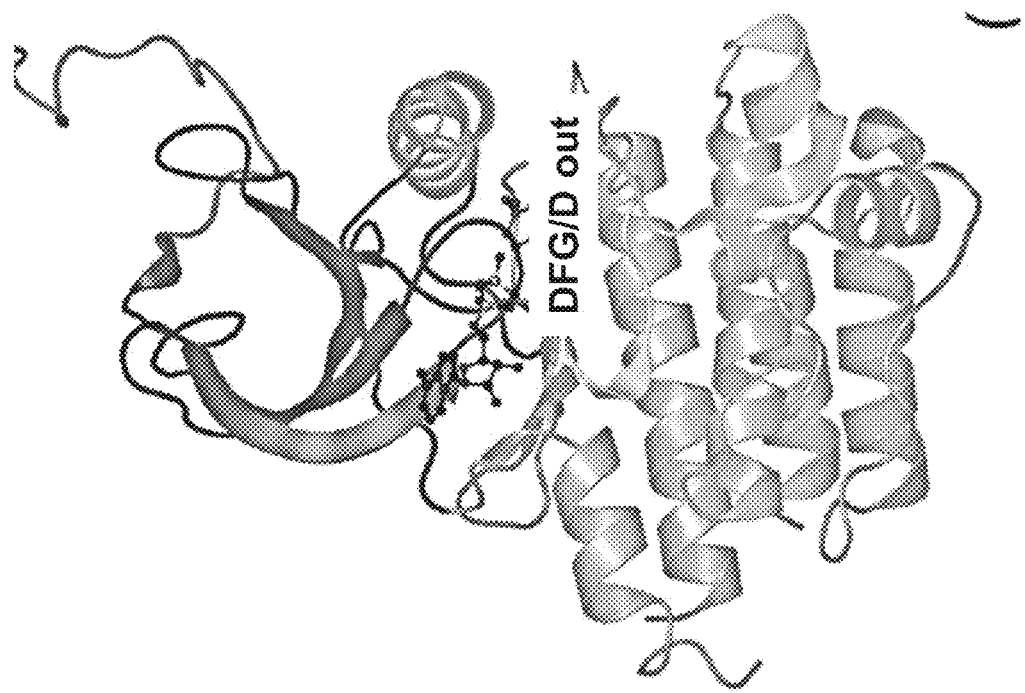
Figure 10C:
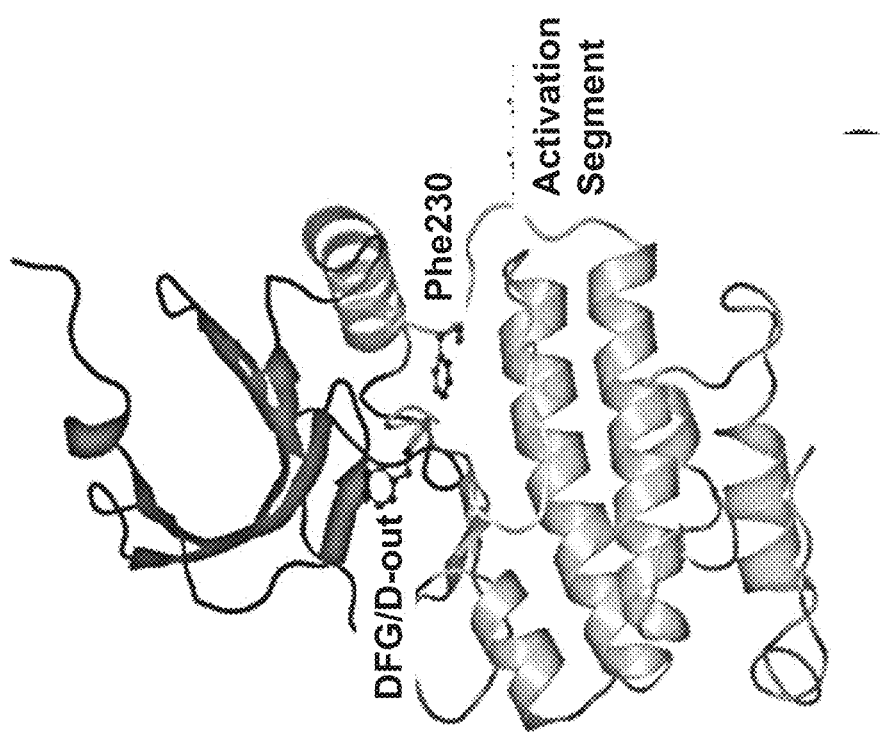
Figure 10B:
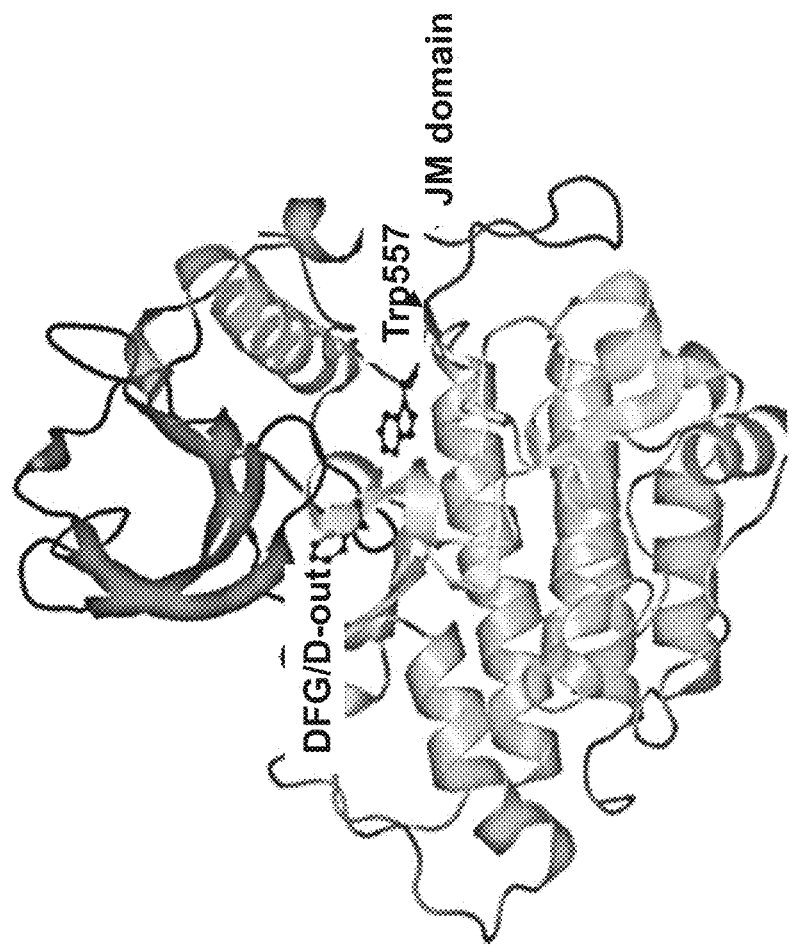

It has been found that the latter pocket serves as binding site for the phenylalanine of the DFG/D motif in active state kinases (FIGS. 10A-10C). This active DFG/D motif conformation is referred to as DFG/D-in conformation and its corresponding binding site will henceforth be referred to as DFG/D-in pocket. In Mnk-1, however, the presence of Phe230 in the DFG/D-in pocket restricts the access for the DFG/D motif and induces the inhibitory DFG/D-out which sterically blocks the ATP binding site (see next paragraph). The reconstructed activation segment in particular Phe230 thus constitutes an autoinhibitory element which plays a key role of a Mnk specific regulatory mechanism.

Hitherto, the blockade of the DFG/D-in pocket as a means of an autoinhibitory strategy has been seen in c-KIT and Flt3, two closely related type III receptor tyrosine kinases. c-KIT and Flt3 contain a juxtamembrane (JM) domain located N-terminally of the kinase which autoinhibits 'in trans' by induction of DFG/D-out (Griffith et al., Mol. Cell. (13) (2004) 169-178; Mol et al., J. Biol. Chem. (279) (2004a) 31655-31663). In both cases residues emanating from the JM domain (Leu576 in Flt3 and Trp557 in c-KIT) are plunged into DFG/D-in pocket which forces the DFG/D motif into the inhibitory DFG/D-out conformation (FIGS. 10A and 10B). Consequently, Mnk-1 executes an autoinhibitory mechanism which is analogous to c-KIT and Flt3 but makes use of a different structural element (FIG. 10C). Mnk-1 (SEQ ID NO.: 18) employs its reconstructed activation segment and Phe230 to silence its activity instead of the JM domain, which occurs in c-KIT and Flt3, to keep the DFG/D-in pocket engaged (FIG. 10C).

Also in case of Mnk-I, the data provided by the present invention allow for the determination of a DFD-in-pocket. This pocket is defined, in particular, by Leu98 and Thr97, His168, Ile107, Ile189 and Leu161, as described above. By occupying said DFD-in-pocket, the DFD motif is at least partially located in the ATP pocket, thus, inhibiting ATP binding by the Mnk. Thus, blocking the DFD-in-pocket results in an inhibition of the kinase activity. Therefore, a further aspect of the present invention is the provision of molecules which bind to the DFD-in-pocket and, thus, inhibit Mnk. Since autoinhibition of Mnk-I by the activation segment, in particular, occurs by the location of Phe230 of the 12 insert of the activation segment into the DFD-in-pocket, suitable inhibitors may comprise the whole or partial sequence of the activation segment of Mnk-I consisting of amino acids 191 to 240 and, in particular, comprising the sequence of insertion 12 consisting of amino acids 228 to 232. Suitable peptides, for example, are (223) APEVVEVFTDQA(234) (SEQ ID NO.: 16) or (225)EVVEVR(231) (SEQ ID NO.:17).

The vast majority of protein kinases bear an Asp-Phe-Gly (DFG) motif at the beginning of the activation segment (subdomain VII) which shapes the 'lip' of the ATP binding 'mouth' of protein kinases at the interlobal cleft (Hanks, Genome Biol. (4) (2003) 111; Hanks, Science (241) (1988) 42-52; Taylor, Structure (2) (1994) 345-355). The first aspartate of this motif is invariant among catalytically active protein kinases and is known to coordinate a magnesium ion essential for phosphate transfer (FIG. 11A) (Adams, Chem. Rev. (101) (2001) 2271-2290). The DFG motif is thus referred to as magnesium binding loop.

Mnk's, however, bear an Asp-Phe-Asp (DFD) motif at the corresponding position. As a result of the DFG/D-in pocket blockade by Phe230 (of the amino acid sequence according to SEQ ID NO.: 18) the DFG/D motif of Mnk-1 adopts the inhibitory DFG/D-out conformation (FIG. 11B): The DFD motif is rotated by ~180° around the $\Phi$ angle of Asp191 ($\Phi_{Asp191}$=−120) with respect to the DFG/D-in conformation of active state protein kinases (e.g. DAPK1 $\Phi$Asp161=55° FIG. 11A). As a result Phe120 occupies a hydrophobic pocket provided by Val63, Leu108, Phe124 (the gatekeeper residue) and Leu177 (all positions of the amino acid sequence according to SEQ ID NO.: 18) which would normally accommodate the adenosyl moiety of ATP. The DFG/D-out conformation has also been described above for Mnk-2.

Thus, since both Mnk-1 and Mnk-2 display this feature, the adoption of DFG/D-out is the default state of inactive Mnk kinases and distinguishes them from most other Ser/Thr kinases which exhibit the active DFG/D-in conformation in their unligated form.

In Mnk-1, the DFD motif participates in an ionic network that explains the preference for the DFG/D-OUT conformation. Both, the invariant Asp191 and the Mnk specific Asp193 (of the amino acid sequence according to SEQ ID NO.: 18) are engaged in tight acid-acid sidechain interactions with active site residues (FIG. 11B):

(i) Asp191 binds to Glu94;
(ii) Asp193 binds to Asp170.

Glu94 and Asp170 (of the amino acid sequence according to SEQ ID NO.: 18) correspond to residues which are invariant among catalytically active protein kinases (Hanks, Science (241) (1988) 42-52). Glu-94 emanates from the regulatory helix αC and known to form an ion pair with Lys78-Glu94 which is necessary for productive ATP binding (Adams, Chem. Rev. (101) (2001) 2271-2220). This pairing is obstructed in Mnk-1 since Asp191 of the DFG/D motif interacts with Glu94 (OD-Asp191: OE-Glu94) as well as with Lys78 (O-Asp191:Nz-Lys78). Asp170, which interacts with Asp193, corresponds to the catalytic aspartate of the C-loop.

Although acid-acid sidechain interactions appear unusual on the first glance interaction between acid side chains are often observed in protein structures and are particularly abundant within the catalytic center of enzymes (Flocco, J. Mol. Biol. (254) (1995) 96-105). The pH of the crystallization conditions (pH 5.6) may have favored the stabilization of those interaction but they have been observed even in basic environments which suggests strong alterations of the local pKa (Flocco et al., ditto). The O—O distances between the two carboxylic acid groups reside in proximity of 2.6 Å and 2.5 Å which is significantly shorter than the O—O distance between non-acidic hydrogen donor/acceptor pairs. The latter observation been attributed to a proton sharing binding mode (Flocco et al., ditto). As described for other such acid-acid interactions Asp191:Glu94 as well as Asp193:Asp170 (of the amino acid sequence according to SEQ ID NO.: 18) are stabilized by amines (Lys78) or amides (Asn175), respectively (see e.g. (Werten, J. Biol. Chem. (277) (2002) 45502-45509) for comparison).

The activation segment embodies the structural elements of protein kinase domains which displays the strong conformational plasticity and is often structurally modified by upstream regulators (Huse, Cell (109) (2002) 275-282). In most protein kinases the flexible portion of the activation segment is restricted to a stretch, called the activation loop, which is located between the DFG/D motif and the so called P+1 loop (Nolen, Mol. Cell. (15) (2004) 661-675). The P+1 loop is known to interact with the residue adjacent to the phosphorylation site of substrate peptides and plays therefore an important role in substrate peptide positioning (Knighton, Science (253) (1991) 414-420).

Within the Mnk subfamily, however, the activation segment is prolonged with respect to other CaMK group kinases by two amino acid insertions (FIGS. 8A and 8B) and the stretch which is subjected to conformational plasticity is strongly expanded. The flexible portion not only includes the activation loop but also the P+1 loop, the region corresponding to the short helix α-EF and the α-EF/αF loop. Both of the activation segments, the P+1 loop and α-EF, occupy conserved sites in the vast majority of reported protein kinase structures. In Mnks, however, this region unfolds and adopts an extended conformation which differs between Mnk-1 and Mnk-2. Hence, the activation segment within the Mnk subfamily is expanded an encompasses a flexible 45 amino acid stretch that spans the region from Magnesium binding DFD motif (DFG in other kinases) up to helix αF (FIG. 8B).

Autoinhibition is a prominent strategy of protein kinase regulation which is imposed differently in individual cases and may affect various functional sites of the molecules. Regulatory domains which locate to regions outside the core of the protein kinase domain are, for example, employed in CaMKI (Goldberg, Cell (84) (1996) 875-887), Twitchin (Kobe, Embo J. (15) (1996) 6810-6821) and c-KIT (Mol, J. Biol. Chem. (279) (2004a) 31635-31663).

In the case of c-KIT and Flt-3, two type III receptor tyrosine kinases, an N-terminal JM domain autoinhibits by inducing the DFG/D-out conformation and, thus, blocking ATP binding. Mnk-1 is likewise autoinhibited by the induction of the DFG/D-out conformation. In contrast to c-KIT and Flt-3, however, where the JM domain mediates autoinhibition in trans', Mnk-1 induces DFG/D-out through a reconstructed activation segment and inserts Phe230 into the DFG/D-in pocket, which usually accommodates the DFG/D-Phe. Hence, the activation segment of Mnk-1 acts as an internal autoinhibitory domain in analogy to the JM domain of c-Kit and Flt-3. The structures of Mnk-1 (SEQ ID NO.: 18) and Mnk-2 (SEQ ID NO.: 19) highlight the significance of the DFG/D-motif for protein kinase regulation. To date, the DFG/D-OUT conformation has been observed in only a fraction of the ~50 protein kinases for which structural data are available.

Notably, for the development of protein kinases inhibitors the DFG/D-out conformation is of importance. In certain small molecule inhibitor:kinase complex structures the DFG/D-out conformation is stabilized and/or induced as in, such as in the Birb796:p38 (Pargellis, Nat. Struct. Biol. (9) (2002)

269-272), Cleevec:c-Abl (Nagar, Mol. Cell (15) (2004) 661-675) and AAL-993:VEGFR-2 (Manley, Biochem. Biophys. Acta (1679) (2004) 17-27), which causes the inactivation of the enzyme. The structures of Mnk-1 and Mnk-2 provide evidence that the adoption of DFG/D-out is a common strategy of kinase regulation which is not restricted to certain phylogenetic groups.

The invention further relates to a model of Mnk activation which comprises 4 states:
(I) the inhibited state,
(II) the intermediate state,
(III) the primed state,
(IV) the active state (FIG. 12).

Figure 12:
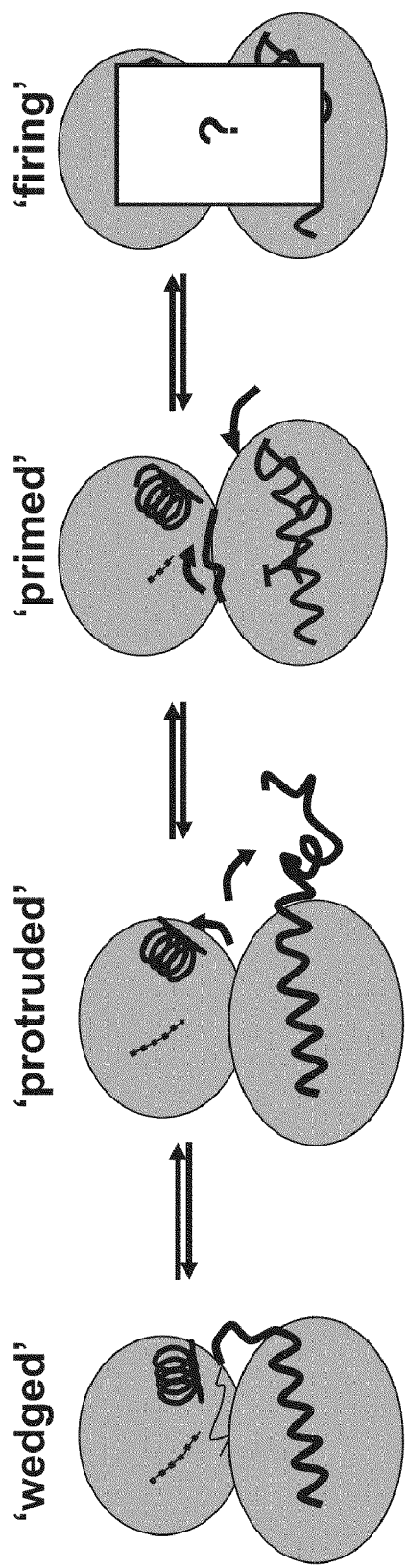
Figure 13A:
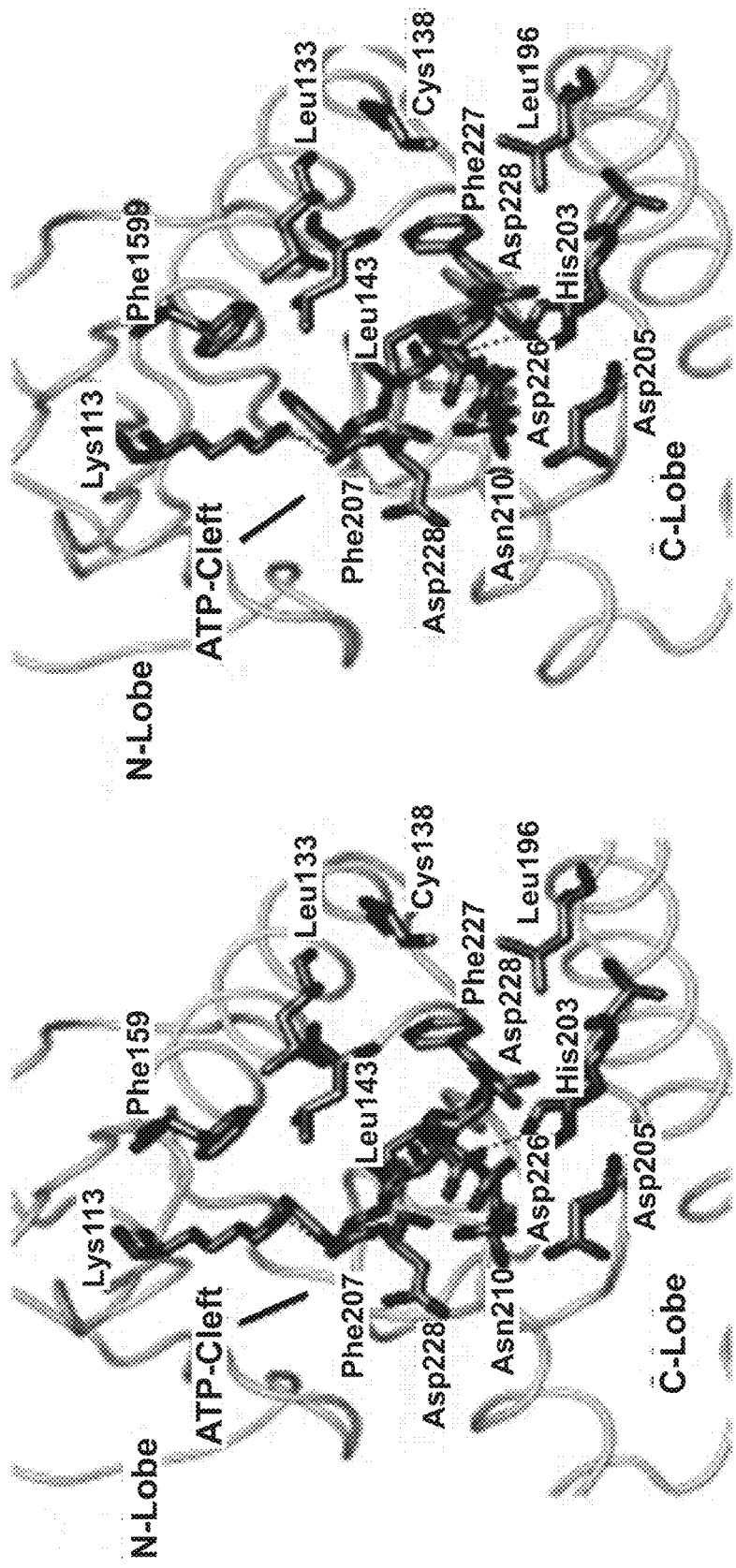
Figure 13B:
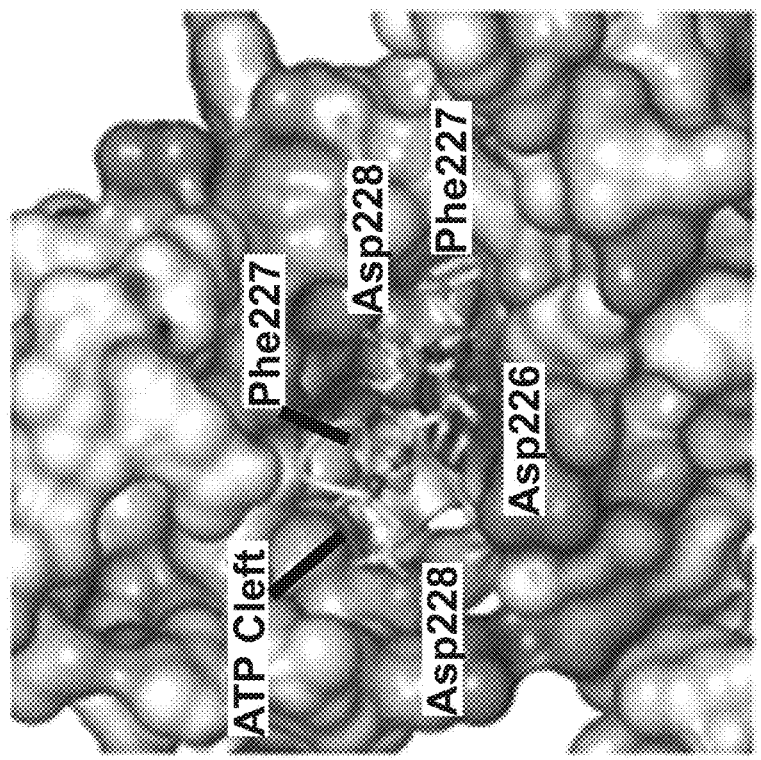
Figure 13B:
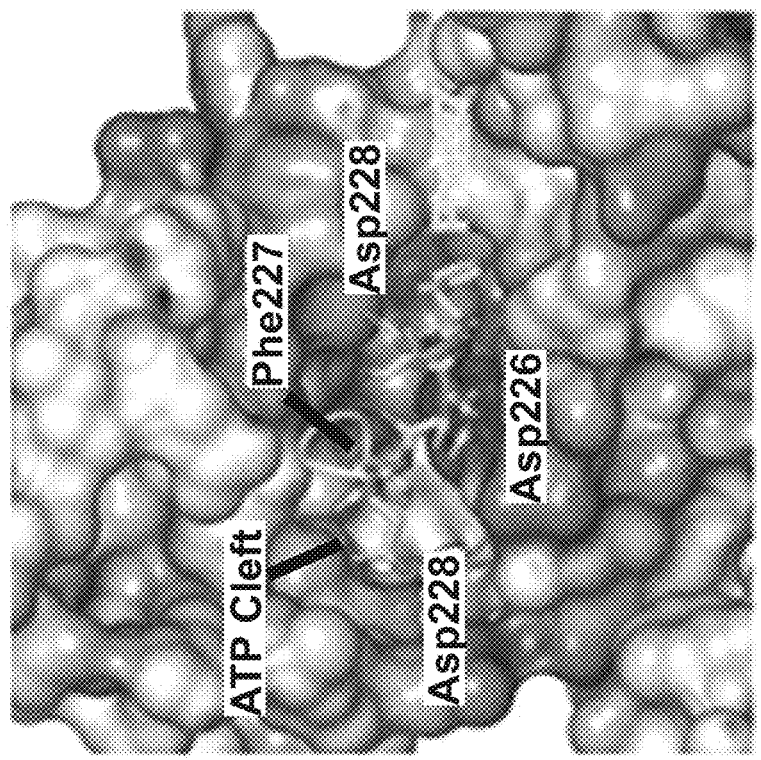
Figure 13C:
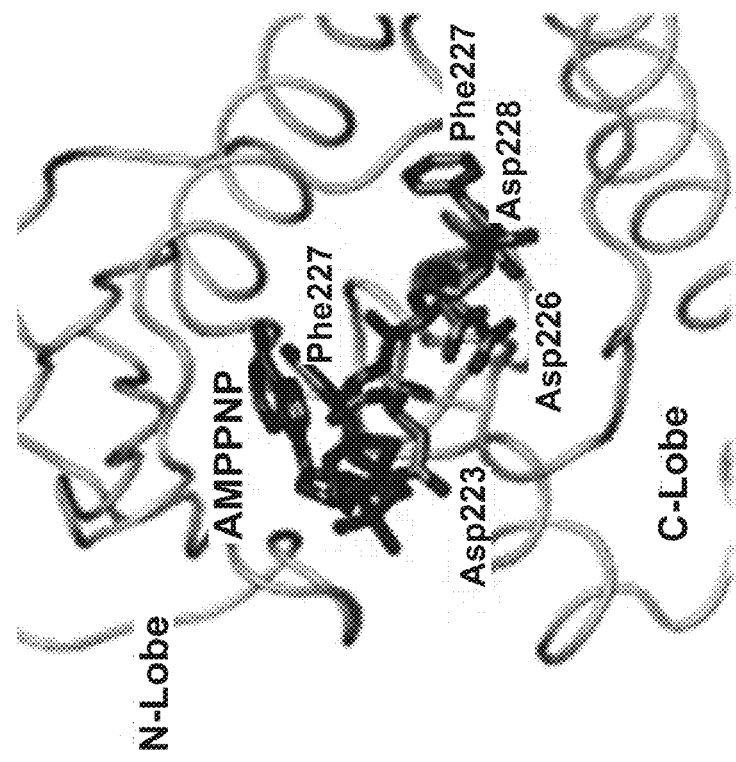
Figure 13C:
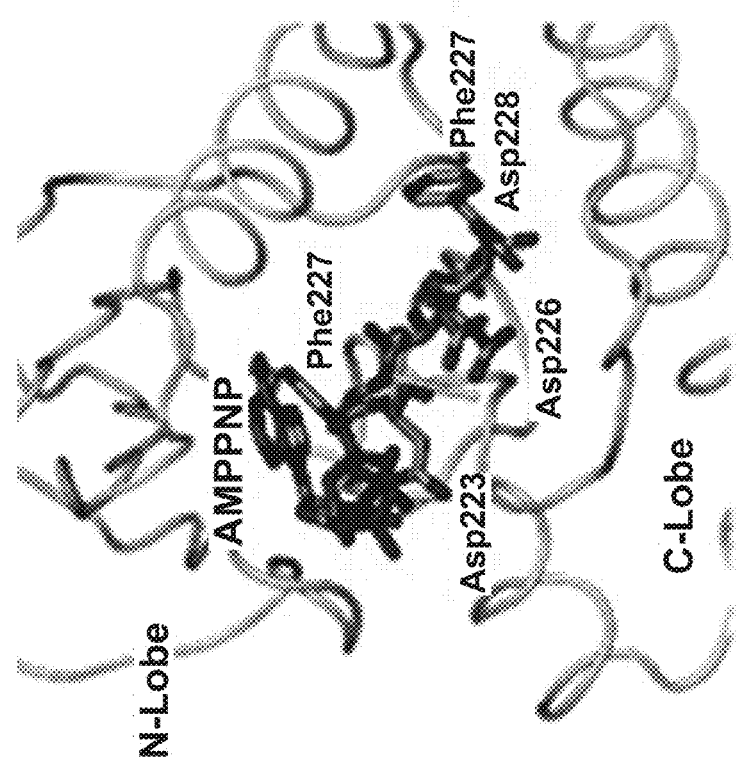
Figure 13D:
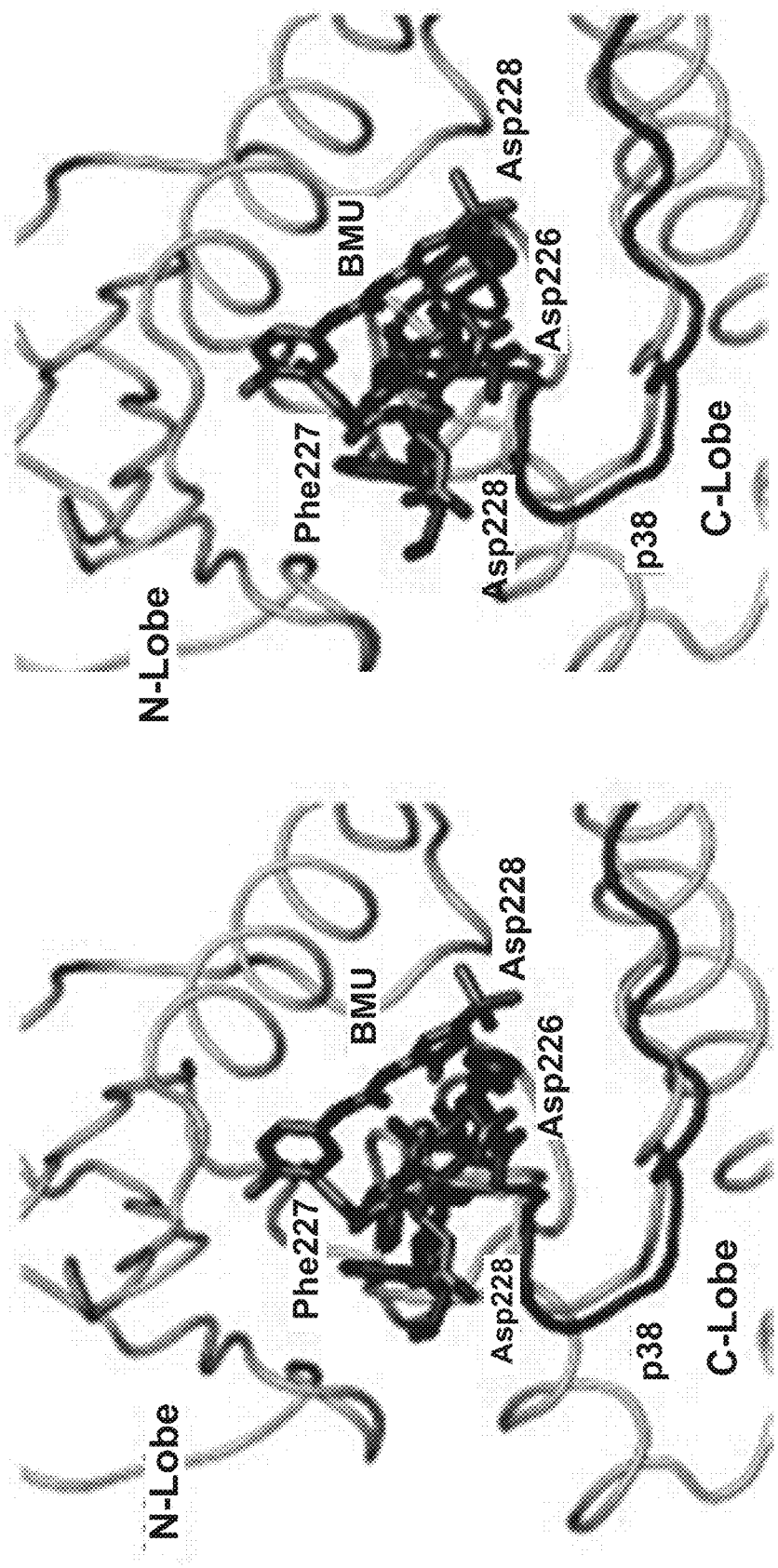

Without wishing to be bound by theory, the states I and II are represented by the structures of Mnk-1 (SEQ ID NO.: 18) and Mnk-2 (SEQ ID NO.: 19), respectively, state III can be modeled based on the Mnk-2 mutant structure and other active state kinases and state IV is hypothetical (FIG. 12). The sequential interconversion requires pronounced topological rearrangements which affect the activation segment, the N-lobe and the ATP binding site. The hallmarks of state I are the induction of the DFG/D-out conformation as well as lobe closure and αC displacement induced by a novel positioning of the reconstructed activation segment. State II is enabled by the protrusion of the activation segment and leads to the opening of the interlobal cleft mainly by repositioning of helix αC and, as a result, to the formation of the essential Lys-Glu ion pair. However, state II displays still several features of inactive state kinases, e.g. the DFG/D-out conformation, and thus requires further structural rearrangements.

An inward switch of the activation segment is required enabling the formation of conserved intramolecular contacts, for example the interaction of the catalytic base aspartate (Asp-170) with Ser/Thr residue from the P+1 loop (Ser218). In addition the magnesium binding loop has to switch into the DFG/D-in position and remove the ATP pocket blockade as seen in the Mnk-2 mutant structure (SEQ ID NO.: 21). The structure of Mnk-2 does furthermore proof, that Mnk's do not have lost the potential to fold a generic α-EF helix and a P+1 loop, a region which is completely unwound in Mnk-1. The activation loop of Mnk's, which bears the two phosphorylation sites which are targeted by upstream kinases (Waskiewicz, dito), is likely stabilized by phosphorylation as seen in many kinases (Johnson, Cell (85) (1996) 149-158; Nolen, Mol. Cell. (15) (2004) 661-675).

Resembling other instances a primary phosphorylation event could stabilize the activation loop conformation by interacting with the basic RD-pocket which is thereby neutralized and disrupts the interaction of the RD-Arg and Asp-238 (Asp-273 in Mnk-2 (SEQ ID NO.: 19) which could, in turn, destabilizes the open conformation of the more distal parts of the activation segment. Sequentially, the secondary phosphorylation could further alter the activation loop conformation which, in turn, induces a lobe closure by brining the Glu-Lys ion pair closer to the ATP binding cleft in analogy to state I but in absence of the inhibitory DFG/D-out conformation. To this end the newly introduced negative charge of the secondary P-site could provide a pulling force by interacting with basic residues such as Arg90 and Arg93 and substitute for the roles Glu225 and Glu228 in the wedged state, which held αC in place. In summary, the conversion between the states II/III and/or III/IV requires phosphorylation. The primary phosphate stabilizes the primed state III by interacting with, for example, the RD-Arg and the secondary phosphorylation further stabilizes the substrate receiving activation segment configuration and promotes lobe re-closure by interaction with the αC helix.

Helix α-EF and the P+1 loop are unwound in Mnk-1 (SEQ ID NO.: 18) which culminates in a complete reconstruction of the activation segment. Mnk-1 is autoinhibited on several levels. The activation segment entails this inactivity by two cross talking series of structural changes. Firstly, it induces an ATP pocket blockade by inducing a DFG/D-out conformation and, thus, indirectly communicates with the Lys-Glu pair and the N-lobe. Secondly, it induces a pseudo-active closed conformation of the N-lobe by interacting with helix αC.

The present Mnk-1 structure (SEQ ID NO.: 18), thus, reveals novel aspects of kinase architecture and regulation which can be used for rational inhibitor design.

Especially preferably, the present invention relates to crystalline human Mnk-1 protein. Mnk-1 is a human protein kinase which targets the translational machinery via phosphorylation of the eukaryotic initiation factor 4E (eIF4E).

The invention further relates to crystalline human Mnk-1 (SEQ ID NO.: 18) protein having a three-dimensional structure defined by all or a selected portion of the structural coordinates shown in Table 3. The coordinates shown in Table 3 were obtained as described in the Examples herein.

| Data collection and refinement statistics | |
|---|---|
| | Mnk-1-KR wildtype (SEQ ID NO.: 18) |
| Data Collection | |
| Space group | P4$_3$2$_1$2 |
| Cell dimensions | |
| a, b, c, (Å) | 93.5, 93.5, 175.2 |
| α, β, γ, (°) | 90, 90, 90 |
| Resolution (Å) | 30.0-2.8 |
| R$_{sym}$ or R$_{merge}$ | 10.3 (34.1) |
| // σ/ | 9.9 (1.9) |
| Completeness (%) | 89.8 (43.0) |
| Refinement | |
| Resolution (Å) | 30.0-2.8 |
| No. reflections | 17771 |
| R$_{wock}$/R$_{ros}$ | 23.0/28.3 |
| No. atoms | |
| Protein | 2905 |
| Water | 19 |
| β-factors | |
| Chain A | 38.12 |
| Chain B | 60.17 |
| Waters | 28.1 |
| R.m.s deviations | |
| Bond lengths (Å) | 0.007 |
| Bond angles (°) | 1.1 |

The crystalline human Mnk-1 protein (SEQ ID NO.: 18) preparations according to the invention can be prepared, for example, by
i. expression of human Mnk-1 protein in cells, e.g. in *E. coli*,
ii. lysing the cells to recover crude Mnk-1 protein preparation,
iii. purifying the crude Mnk-1 protein preparation, e.g. by affinity tag chromatography, and
iv. crystallizing the purified human Mnk-1 (SEQ ID NO.: 18) protein, e.g. by vapor diffusion.

The crystalline preparation of human Mnk-1 protein, in particular, of the kinase region of human Mnk-1 protein according to the invention can be used for the generation of crystal structure data of human Mnk protein. In particular, binding sites or interaction sites with ligands, especially inhibitors or substrates, can be obtained thereby. Further, it is possible to identify binding sites to maintain the proteins in active or inactive form. In particular, the results presented herein for Mnk-1 protein also allow for identification of ligands.

The crystalline preparations according to the invention, preferably, are single crystals and, more preferably, crystals having an edge length of at least 1 µm, more preferably, at least 10 µm and, most preferably, at least 50 µm. The crystals preferably are arranged in such a manner that X-ray structure analysis can be carried out. Therefore, another subject matter of the invention is a crystal structure of human Mnk-1 protein defined by all or a selected portion of the structural coordinates shown in Table 3.

Using the crystalline human Mnk-1 (SEQ ID NO.: 18) protein and the crystal structure, respectively, Mnk-1 protein ligands can be designed, identified or prepared. Moreover, it is possible to identify regulatory mechanisms for protein kinases as described above. For identifying ligands or regulatory mechanisms, in particular, computer-aided modeling programs are used.

In addition to the computer-assisted screening for identifying ligands, a method as described in WO 03/037362 is preferably applied to actually identify and verify ligands.

The invention further relates to ligands, in particular, substrates or inhibitors of Mnk-1 protein of isoforms thereof as well as of other protein kinases obtained by using the crystalline preparations or crystal structures. Such ligands preferably are active agents in pharmaceutical compositions. Said pharmaceutical compositions, in particular, can be used for treating diseases, in the case of which manipulation or especially inhibition of Mnk-1 proteins is desirable such as, for example, metabolic disorders such as obesity, diabetes and the metabolic syndrome as well as cancer.

The results and data presented show that the DFG/D-in pocket (including Phe 230 in Mnk-1) can serve as a general inhibitor binding site. This inhibitor is not restricted to Mnk's. Therefore, the invention also relates to an inhibitor binding site comprising a DFG/D-in pocket.

The invention is further illustrated by the attached Figures as well as the Examples given below.

(FIGS. 1A and 1B): Mnk2 Organization and Sequence Alignment.

(FIG. 1A) Schematic comparison of the two splice variants of human Mnk2 indicating the arrangement of functional domains (as labeled). The region investigated herein (Mnk2 kinase region, Mnk2-KR) is boxed. Alternative splicing does neither affect the N-terminus nor the kinase domain. NLS—nuclear localization signal. eIF4G—eukaryotic initiation factor 4G, the scaffolding protein of the translation initiation complex which binds Mnk1 and Mnk2 (Pyronnet et al., 1999; Scheper et al., 2001).

(FIG. 1B) Sequence alignment of the kinase domains of human Mnk1 (SEQ ID NO.: 4) and Mnk2 (SEQ ID NO.: 9), the *Drosophila* and *C. elegans* Mnk orthologs (Lk6 (SEQ ID NO.: 5) and R166.5 (SEQ ID NO.: 6), respectively) and three human CaMK group kinases (MAPKAP) (SEQ ID NO.: 7); DAPK1 (SEQ ID NO.: 8); and CAMK1a (SEQ ID NO.: 3) of known structure (MAPKAP—MAP kinase-activated protein-kinase). Mnk2 (SEQ ID NO.: 9) numbering refers to a recently reported sequence (Slentz-Kesler et al., 2000). Secondary structure elements as found in Mnk2-KR are indicated below the alignment. Stars indicate phosphorylation sites (Scheper et al., 2001). The catalytic loop (i); the DFD motif (DFG in other kinases) (ii); and the P+1 loop (iii) are marked with open bars. Insertions characteristic for Mnks are boxed (I1-13). Open circles mark Gly91 and Gly93 of the glycine rich loop, Lys113 and Glu129 known to be important for ATP binding (Taylor and Radzio-Andzelm, 1994), filled circles mark Gly164 and Gly165 of the hinge region separating the N-terminal and C-terminal lobes.

FIGS. 2A-2D: Overall topology of the Mnk-2 kinase domain. Structural parts outside the core of the kinase domain were deleted. Structures of the apoenzymes of CAMK1 (SEQ ID NO.: 3) (FIG. 2A, 1a06.pdb), DAPK1 (SEQ ID NO.: 8) (FIG. 2B, 1jks.pdb) and MAKPKAPK2 (SEQ ID NO.: 7) (FIG. 2C; 1kwp.pdb) were superimposed onto Mnk-2 (SEQ ID NO.: 9) (FIG. 2D) and are shown on similar orientation. Parts which cannot be traced in the electron density are represented by dashed lines.

Figure 3A:
Figure 3B:
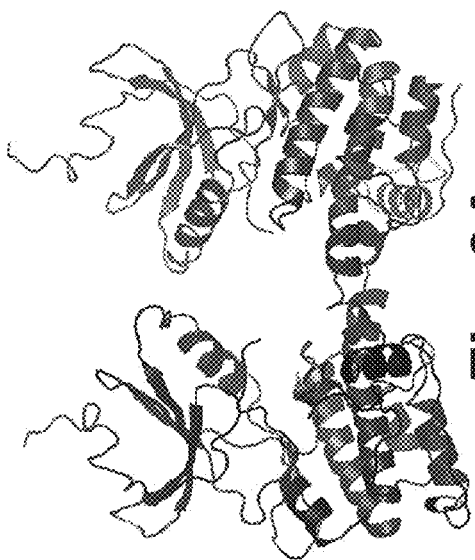
Figure 3C:
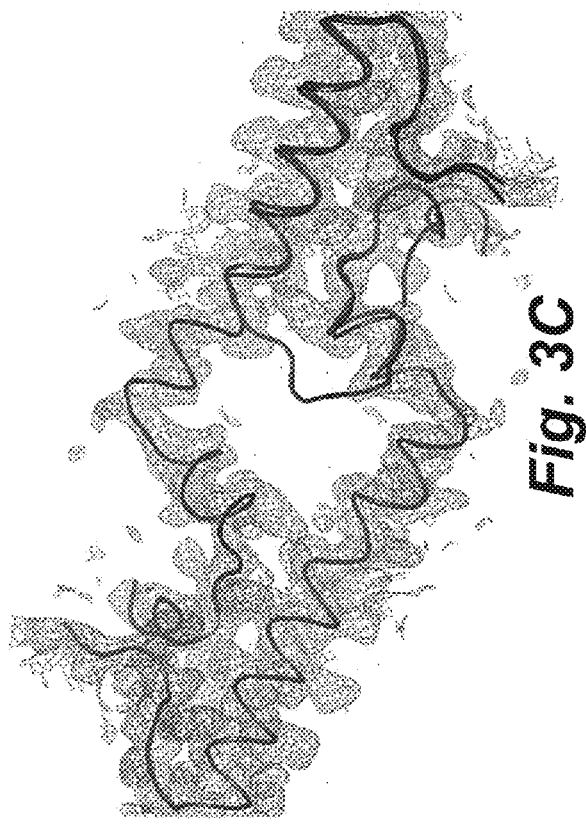

FIGS. 3A-3C: Open conformation of the activation segment. Two symmetry equivalent Mnk-2 molecules, dark and light, are shown in FIG. 3A. The same molecules are shown from top after rotation by 90° (FIG. 3B). FIG. 3C shows the 2Fo-Fc electron density contoured at 1σ and the conformation of the same region of DAPK1 (black).

Figure 4A:
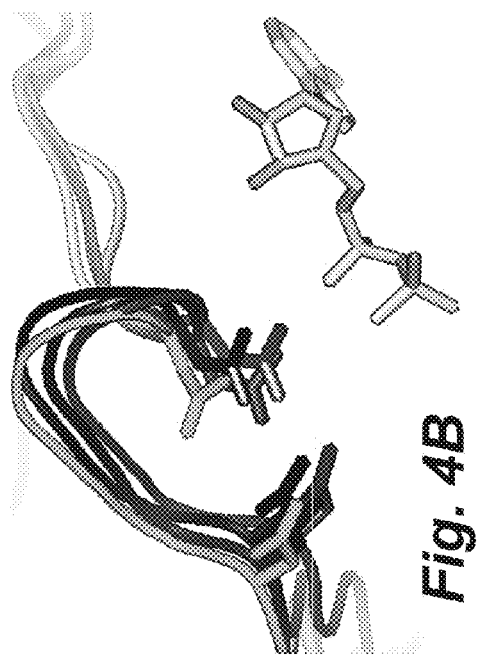
Figure 4B:
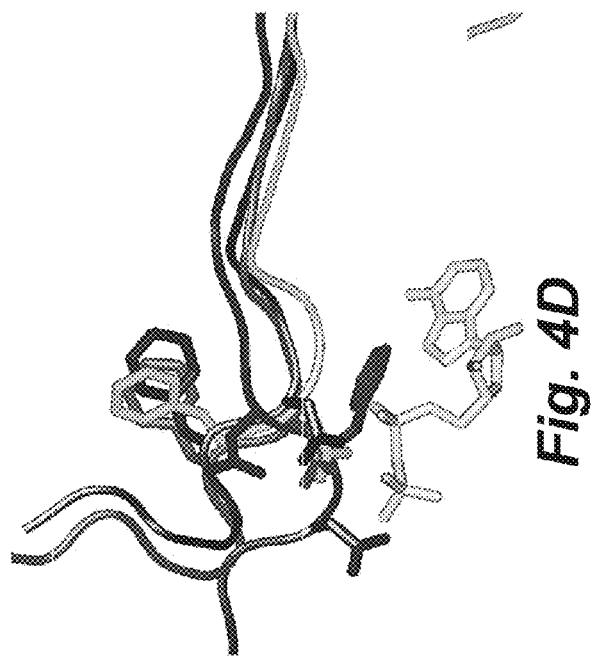
Figure 4C:
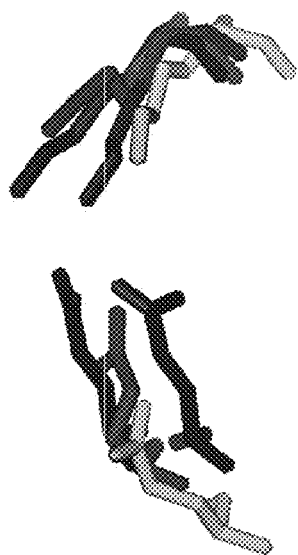
Figure 4D:
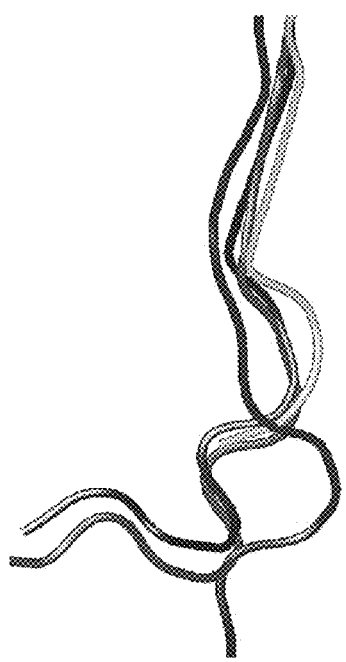

FIGS. 4A-4D: Conformation of the ATP binding pocket. Regions with importance for catalysis from Mnk-2, MAP-KAP2, CaMK1 and DAPK1 are shown. FIG. 4A shows Lys113 and Glu 129 (Mnk-2 numbering). In FIG. 4B the backbone of the C-loop and the side chains of Asp205 and Asn210 are displayed together with ADP from the MAP-KAP2/ADP co-structure (1 ny3.pdb). FIG. 4C shows the backbone around the DFG(DFD) motif and FIG. 4D includes the side chains of this region and the ADP from FIG. 4B.

Figures 5A, 5B:
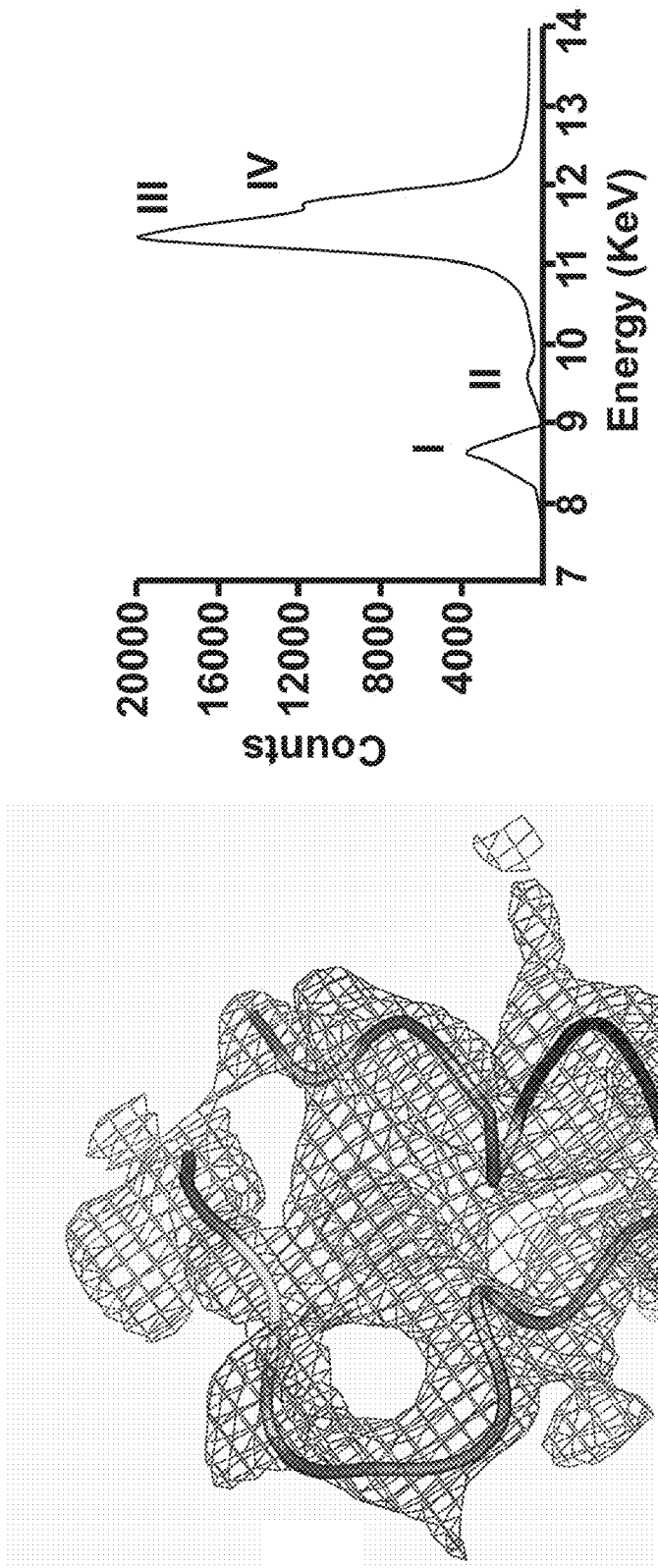

FIGS. 5A and 5B: Zinc binding site. (FIG. 5A) The region of putative zinc site in Mnk-2 is shown as backbone plot together with a 2Fo-Fc map contoured at 1σ and a DANO map contoured at 5σ. The region is highly flexible in our crystals and the region from Trp305 to Glu309 (SEQ ID NO.: 19) lacks clear backbone density. (FIG. 5B) X-ray emission spectrum of native Mnk-2 crystals with peaks corresponding to I=ZnKα line, II=ZnKβ line, III compton scattering, IV elastic scattering.

Figure 6A:
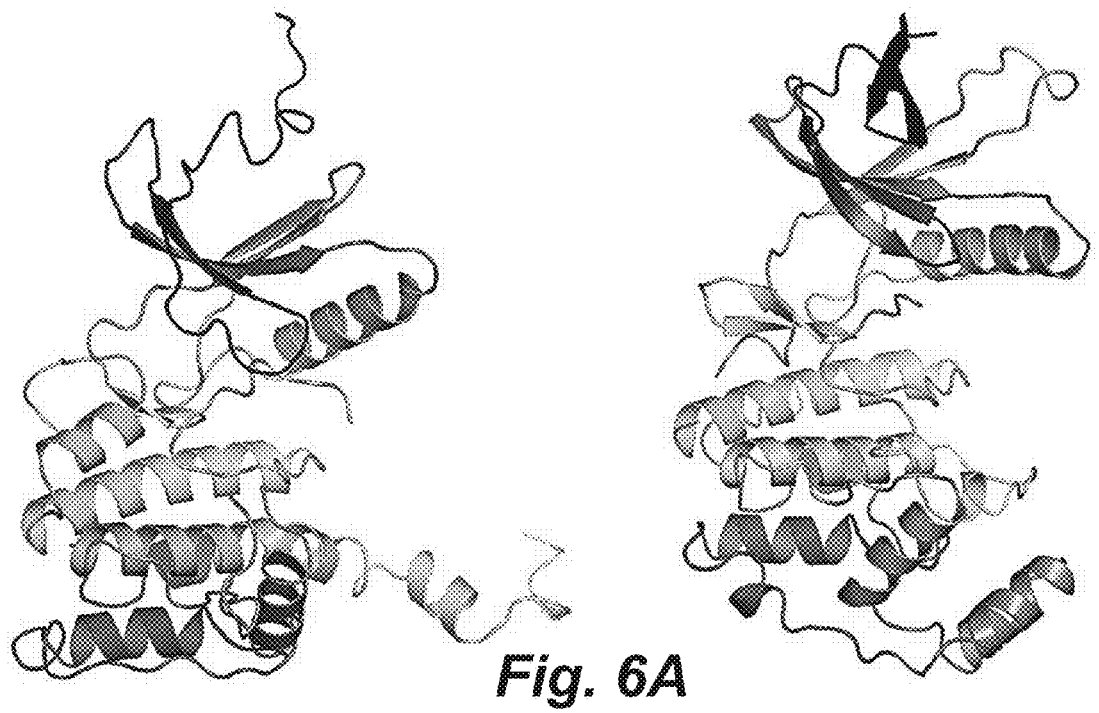
Figure 6B:
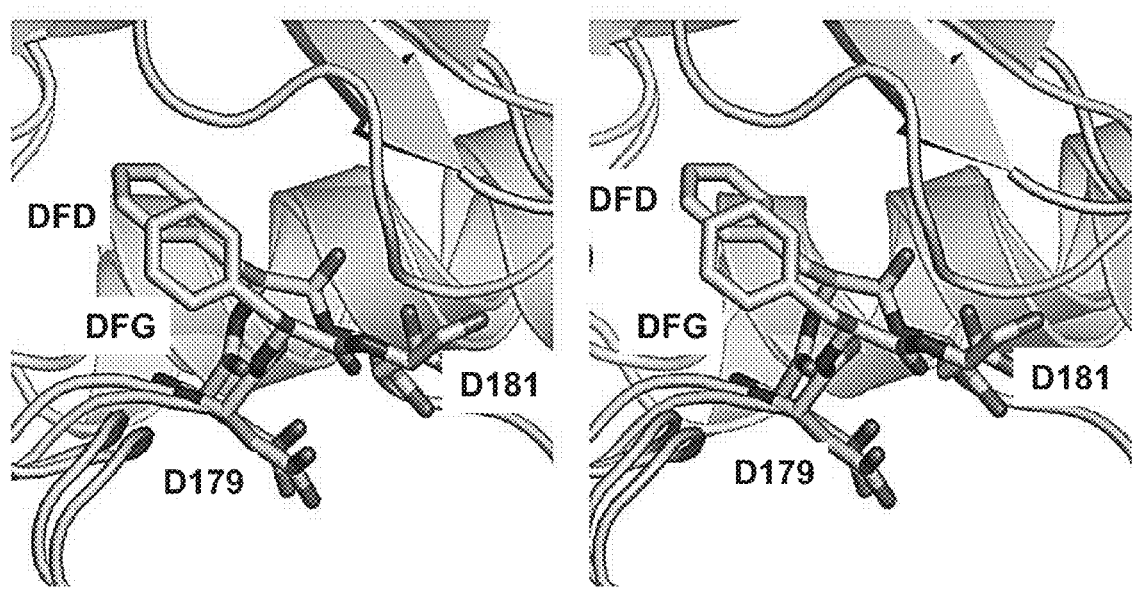

FIGS. 6A and 6B: Comparison of Mnk-2 Kinase Domain and p38.

FIG. 6A. Ribbon plots of Mnk-2 kinase domain (left) and p38 (right; PDB ID 1KV1) in the same orientation. The molecules demonstrate the same overall structural organization as also observed in other protein kinases.

FIG. 6B Stereo plot of the DFD/DFG regions after best-fit global alignment of the two proteins. The DFD/DFG motifs are shown as stick figures. Aspartates 226 and 228 of Mnk-2 are labeled to indicate the direction of the polypeptide chain. The surrounding structural elements are shown as ribbons. The atypical DFG-conformation of p38 is induced by binding of diaryl urea type inhibitors (not shown; PDB IDs 1KV1 and 1KV2). Mnk-2 adopted a similar conformation spontaneously in the present crystals. The diaryl urea class of inhibitors bind between the DFG motif of p38 and the helix shown in the background. The DFD motif of Mnk-2 (SEQ ID NO.: 19) is even further displaced towards the inhibitor binding pocket, suggesting that it could be similarly trapped in the present conformation by an inhibitor.

FIGS. 7A-7C: Model of Inhibitor Binding to Mnk-2 Kinase Domain.

FIG. 7A. Overview of the Mnk-2 kinase domain in complex with a diaryl urea-based inhibitor (1-(5-tert-butyl-2-methyl-2H-pyrazol-3-yl)-3-(4-chloro-phenyl)-urea; BMU; PDB ID 1KV1). Mnk-2 is displayed according to its secondary structure elements, the DFD motif and other Mnk-2 residues contacting the drug are shown as stick figures. The model was generated by best fit superpositioning of the Cα atom positions of the p38-BMU complex (PDB ID 1KV1) and the Cα coordinates of the Mnk-2 kinase domain. The BMU positioning was subsequently adjusted manually to the indicated binding pocket of the Mnk-2 kinase domain. Side chain conformations of some Mnk-2 residues were likewise adjusted to remove bad contacts.

FIG. 7B. Detailed stereo view of an ATP analog (AMP-PNP) from the co-crystal structure of DAPK1 (PDB ID 1IG1) positioned into the nucleotide binding pocket of the Mnk-2 kinase domain. The model was generated by best fit superpositioning of the two protein molecules as described in A. The AMPPNP molecule in standard binding mode is seen to sterically interfere with the DFD motif of Mnk-2 in the present conformation. This finding suggests that productive ATP binding to Mnk-2 requires a rearrangement in the DFD motif. As a corollary, in the present conformation Mnk-2 is inactive in ATP binding. Secondary structure elements as in FIG. 7A.

FIG. 7C. Detailed stereo view of the Mnk-2-BMU complex model. BMU may bind with the tert-butyl group in a hydrophobic pocket and slide its p-chloro-phenyl ring between the aromatic rings of Phe227 (from the DFD motif) and Phe159. Secondary structure elements as in FIG. 7A.

FIGS. 8A and 8B: Overall structure of Mnk-1 in stereo representation (FIG. 8A) and primary sequence (SEQ ID NO.: 4) (b) (FIG. 8B). (FIG. 8B) residues known to be interact with ATP are marked with closed circles, residues comprising the DFG/G-in pocket or DFG/D-out pocket: empty circles. Mnk specific amino acid insertions are boxed and Mnk specific residues with functional relevance are highlighted with an arrow. Phosphorylation sites are indicated with stars.

FIGS. 9A-9C: N-lobe movement induced by the activation segment. Overall structure of Mnk-1 FIG. 9A and Mnk-2 (FIG. 9B), Mnk-1 FIG. 9A comprising residues involved in the N-lobe αC interaction, Phe239 and the DFD motif Phe in the stick representation. Arg90 and Arg93 correspond to residues known to interact with phospho amino acids (Krupa et al., J. Mol. Biol. (339) (2004) 1025-1039). The corresponding residues in Mnk-2 (FIG. 9B) are Phe 265, Arg 123 and Arg 125.

FIGS. 10A-10C: Autoinhibition in c-KIT (FIGS. 10A and 10B) and Mnk-1 (FIG. 10C).

Figure 11A:
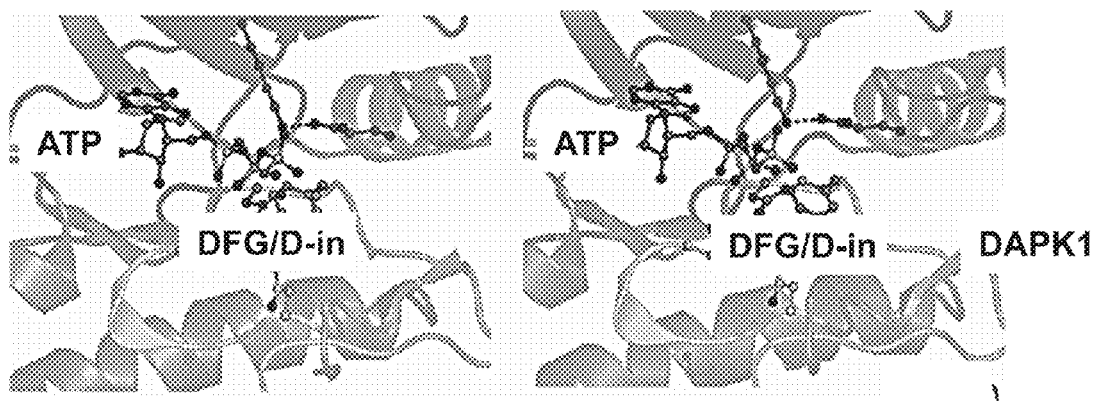
Figure 11B:
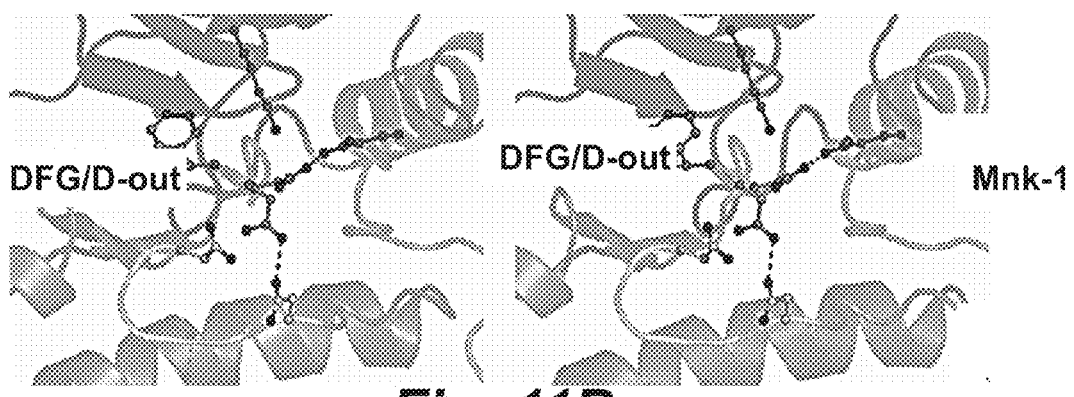
Figure 11C:
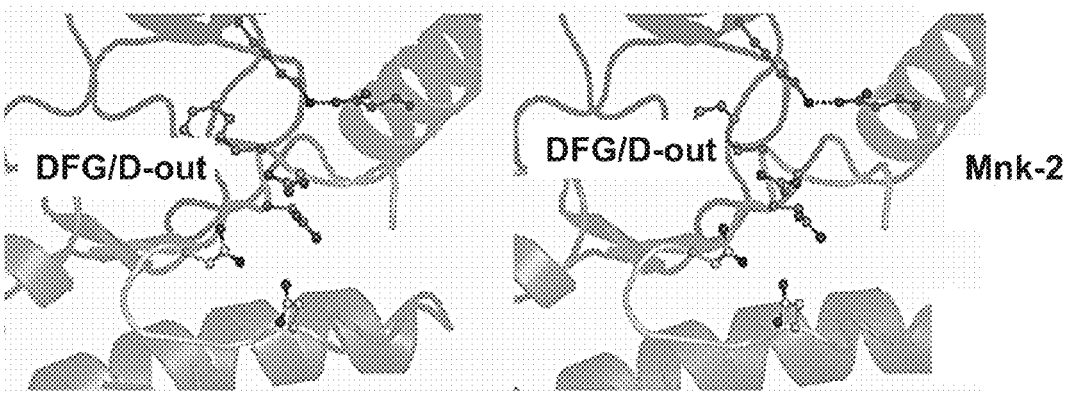

FIGS. 11A-11C: The ATP binding pocket of (FIG. 11A) DAPK1 (1ig1; (Tereshko et al., Nat. Struct. Biol. (8) (2001) 899-907); FIG. 11B Mnk-1; (FIG. 11C) Mnk-2. The molecules are in the same orientation as in FIG. 8A with the ATP binding regions blown up. (FIG. 11A) exemplifies an active state protein kinase of the CamK group and contains the non-cleavable ATP analogon ANP—PNP and $Mn^{2+}$ instead of $Mg^{2+}$ at the functional site. Note the permissive DFG/D-in conformation of the Magnesium binding DFG-motif. The ATP site blockade of Mnk-1 FIG. 11B and Mnk-2 (FIG. 11C) is achieved by the inhibitory DFG/D-out conformation. Mnk-1 FIG. 11B displays acid-acid side chain interactions not present in Mnk-2.

FIG. 12: A Model of the Mnk Activation Cascade.

FIGS. 13A-13D: Neighborhood of the DFD Motif (FIG. 13A) Close-up stereoview of the DFD region and the ATP binding cleft. The DFG/D-OUT conformation of wild-type Mnk2-KR is indicated by a stick representation for Asp226, Phe227, and Asp228 on the upper left with Phe227 and Asp228 poking into the ATP binding cleft. A DFG/D-IN conformation (lower right) has been modeled according to the DFG/D-IN conformation seen in other kinases and as observed for the Asp228Gly mutant of Mnk2-KR (SEQ ID NO.: 21). A backbone trace of Mnk2-KR (SEQ ID NO.: 9) is shown as a semitransparent gray tube. Residues within a radius of 4 Å around the DFD motif in either the DFG/D-IN or -OUT conformations are displayed as sticks. Direct interactions with the protein matrix, which stabilize the DFG/D-OUT conformation, are indicated by dashed lines. Phe227 comes to lie in two different hydrophobic pockets in the two different conformations. No obstacle for adoption of a DFG/D-IN conformation is visible.

(FIG. 13B) Stereoview of the molecular surface of Mnk2-KR (SEQ ID NO.: 9), with the two conformations of the DFD motif as a stick representation. The ATP binding cleft is pointed out. Asp228 in either conformation is well accessible to the aqueous solvent. The DFG/D-OUT conformation not only positions Phe227 and Asp228 in the ATP binding cleft, but also obstructs access to this cleft from the front. The molecule has been rotated by 30° about the horizontal axis (N-terminal lobe to back) relative to (FIG. 13A) in order to afford an unobstructed view into the DFD pockets.

(FIG. 13C) Same view as in (A) with a nonhydrolyzable ATP analog (adenosine 5'-[β,γ-imido]-triphosphate [AMP-PNP]) superimposed as seen in the cocrystal structure with DAPK1 (PDB ID 1IG1). In the DFG/D-OUT conformation, the adenine base clashes with the side chain of Phe227, and the phosphate groups clash with the side chain of Asp228.

(D) The same view as in (FIG. 13A) and (FIG. 13C) with only the DFG/D-OUT conformation shown. The DFG region of a p38-BMU inhibitor complex (PDB ID 1KV1) is shown for comparison (DFG in stick representation; carbon, magenta) as seen after global superpositioning of the protein structures. The BMU inhibitor occupies part of the DFG/D-IN binding pocket and induces a DFG/D-OUT conformation in p38.

Table I shows atom coordinates for the polypeptide having the amino acid sequence of amino acid positions 72 to 369 inclusive of the human Mnk-2 sequence according to SEQ ID NO.: 19. The amino terminus residue Gly70 and Ser71s were cloning artifacts, and atom coordinates for the residues corresponding to the amino acid positions 232 to 250 inclusive and 306 to 309 inclusive of the human Mnk-2 sequence SEQ ID NO.: 19 were not identified.

Table 2 shows atom coordinates for the polypeptide having the amino acid sequence of amino acid positions 72 to 385 inclusive of the human mutant D228G Mnk-2 sequence according to SEQ ID NO.: 21. The amino terminus residues Gly70 and Ser71 were cloning artifacts, and atom coordinates for the residues corresponding to the amino acid positions 229 to 249 inclusive, 306 to 309 inclusive, and 371 to 385 inclusive, of the human Mnk-2 sequence SEQ ID NO.: 21 were not identified.

Table 3 shows atom coordinates for a co-crystal structure of (chain A) the polypeptide having the amino acid sequence of amino acid positions 39 to 335 inclusive of the human Mnk-1 sequence according to SEQ ID NO.: 18 and (chain B) the polypeptide having the amino acid sequence of amino acid positions 41 to 334 inclusive of the human Mnk-1 sequence according to SEQ ID NO.: 18. The atom coordinates for the residues of chain A corresponding to the amino acid positions 197 to 222 inclusive and 261 to 290 inclusive of the human Mnk-1 sequence according to SEQ ID NO.: 18 were not identified. The atom coordinates for the residues of chain B corresponding to the amino acid positions 197 to 222 inclusive and 261 to 298 inclusive of the human Mnk-1 sequence according to SEQ ID NO.: 18 were not identified.

Table 4 shows atom coordinates for a co-crystal structure of the polypeptide having the amino acid sequence of amino acid positions 72 to 371 inclusive of the human mutant D228G Mnk-2 sequence according to SEQ ID NO.: 21 with the generic protein kinase inhibitor staurosporine. The atom coordinates for the residues corresponding to the amino acid positions 229 to 251 inclusive, 300 to 302 inclusive, and 305 to 309 of the human mutant D228G Mnk-2 sequence according to SEQ ID NO.: 21 were not identified.

EXAMPLES

Example 1

Cloning and Purification Mnk-2 and Mnk-1 Kinase Regions

Utilizing techniques known in the art, a cDNA fragment of human Mnk-2 (SEQ ID NO.: 9), corresponding to amino acid residues 72 to 385 inclusive of the human Mnk-2 sequence according to SEQ ID NO.: 19 and encompassing the kinase domain (KD) was amplified using the forward/reverse primer pair 5'CGGGATCCACCGACAGCTTCTCGGGCAGG (SEQ ID NO.:1) 5'ACGCGTCGACCTACCTCTGCAG-GACCATGGAG (SEQ ID NO.:2) (utilized restriction sites underlined) and cloned into the BamHI and SalI sites of the vector pGEX-4T1 (Amersham, Sweden, cat. no. 27-4580-01). This construct allows prokaryotic expression of Mnk-2 kinase region (KR) as fusion protein 15 with a N-terminal, thrombin cleavable glutathione S-transferase (GST) tag.

The amino acid substitution D228G was introduced into the GST-Mnk-2 KR construct employing the Stratagene Quik Change Site Directed Mutagenesis kit according to the manufacturers' instructions. Mutagenesis oligonucleotides were 5'GAAGATCTGT GACTTCGGC CTGGGCAGCG GCAT-CAAACT C (SEQ ID NO.:10) and 5'GAGTTGATG CCGCTGCCCA GGCCGAAGTC ACAGATCTTC (SEQ ID NO.:11). Purification of Mnk-2 KR D228G (SEQ ID NO.: 21) was performed as described for Mnk-2 KR (SEQ ID NO.: 19).

A cDNA fragment of human Mnk-1, corresponding to amino acid residues 37 to 341 and encompassing the kinase domain (KD) was amplified using the forward/reverse primer pair 5'CGGGATCCACTGACTCCTTGCCAGGAAAGI (SEQ ID NO.:12) 5'ACGCGTCGACCTATCCCTTTTCTG-GAGCTTGCC (SEQ ID NO.:13) (utilized restriction sites underlined) and was cloned into the BamHI and SalI sites of the vector pGEX-4T1 (Amersham, Sweden, cat. no. 27-4580-01). This construct allows prokaryotic expression of Mnk-1 kinase region (KR) as fusion protein with a N-terminal, thrombin cleavable glutathione S-transferase (GST) tag.

Expression of GST-Mnk-2 KR or GST-Mnk-1 KR was in *E. coli* BL21 (Merck Biosciences, Germany, cat. no. 69449). Cells were grown in 5 liter flasks with baffle in LB-Bouillon (Merck, Germany, cat. no. 1.10285) supplemented with 100 μg/ml ampicillin (Sigma, Germany, cat. no. A-9518) while shaking with 130 revolutions per minute (rpm) at 37° C. When the culture has reached a density corresponding to an $A_{600}$ of 0.8, an equal volume of ice cold LB/ampicillin is added, the culture transferred to 25° C. and induced for 4 h with 1 mM isopropyl thiogalactoside (Roth, Germany, cat. no. 2316.4). Cells were harvested by centrifugation. Cell pellets were resuspended in 10 ml lysis buffer (50 mM Tris/HCl (Sigma, Germany, cat. no. T-5941) pH 7.5, 200 mM NaCl (Sigma, Germany, cat. no. S-7653), 5 mM DTT (Roth, Germany, cat. no. 6908.2)) per gram wet weight cell pellet. Lysates were prepared by disruption of cells with a Badelin sonoplus sonifier (Badelin, Germany, cat. no. HD207) equipped with a MS72 probe and subsequent clearing in a Sorvall SS34 rotor (Sorvall, Germany, cat. no. 28020) at 18000 rpm/45 min/4° C.

The lysate was applied to two GSTPrep FF 16/10 columns (Amersham, Sweden, cat. no. 17-5234-01) connected in series and equilibrated with lysis buffer. Washes were with 3 column volumes (CV) wash buffer (50 mM Tris/HCl pH 7.5, 100 mM NaCl, 1 mM DTT), 2 CV ATP buffer (50 mM Tris/HCl pH 7.5, 100 mM KCl (Roth, Germany, 6781.1), 20 mM $MgCl_2$(Sigma, Germany, cat. no. M-2670), 5 mM ATP (Sigma, Germany, cat. no. A-7699)) and again 3 CV wash buffer.

Mnk-2 KD was subsequently eluted by on-column thrombin cleavage from the GST tag. In brief, 1000 units of thrombin (Amersham, Sweden, cat. no. 27-0846-01) were dissolved in 60 ml wash buffer and cycled over night at 8° C. over the two columns. The eluate was collected by opening the loop while applying wash buffer to the columns.

The thrombin eluate was diluted 1:5 in 50 mM Tris/HCl pH 8.0 and applied to five 5 ml Q sepharose HP columns (Amersham, Sweden, cat. no. 17-1154-01) connected in series. Elution was with a linear gradient of sodium chloride (50 mM Tris/HCl pH 8.0, 0-1 M NaCl). Fractions were pooled according to purity and concentrated to approx. 16 mg/ml in a 10.000 dalton molecular weight cut-off (MWCO) VivaSpin concentrator (VivaScience, Germany, cat. no. VS0403). The concentrate was transferred into 10 mM Tris/HCl pH 7.5, 50 mM NaCl, 1 mM DTT by gel filtration on a PD10 column (Amersham, cat. no. 17-0851-01). Typical final protein concentration was approx. 12 mg/ml. Aliquots were shock frozen in liquid nitrogen and stored at −80° C. Protein yields were approx. 2 mg of Mnk-2 kinase domain per gram wet weight cell pellet.

After activation by ERK2, the corresponding Mnk kinase regions and full length Mnk proteins show identical activity in a kinase assay based on eIF4e (Ser209) phosphorylation.

2. Crystallization and Data Collection

Initial crystal screening was performed with a MicroSys SQ series 4000/4100 (Cartesian Dispensing Systems) in a 96-well format using a 100 μl reservoir solutions and drop sizes ranging from 200 nl to 1 μl. Crystals used for diffraction studies were grown by vapor diffusion using either hanging or sitting drops at 20° C. The protein solution was mixed with reservoir buffer (100 mM Na-Hepes pH 7.8, 22% polyacrylic acid 5100 and 2% 2-methyl-2,4-pentanediol (MPD) with up to 10-fold excess of protein solution. Crystals were frozen in liquid nitrogen. Diffraction data were collected on the HASY-LAB beamline BW6 (DESY, Hamburg, Germany) at 100 K and λ=1.05 on a Mar-Research (Norderstedt, Germany) CCD detector and process with the HKL package (Otwinowski, Z. and Minor, W. Processing of X-ray diffraction data in oscillation mode. Methods Enzymol. 167, 307-326, September 1997).

3. Structure Determination and Refinement

Initial phases were obtained using the MolRep automated molecular replacement routine from the CCP4 package (Collaborative Computational Project, The CCP4 Suite: Programs for Protein Crystallography. *Acta Cryst. D* 50, 760-763, December 1994) with the death-associated protein kinase (DAPK) as the search model (PDB ID: 1IG1). A mtz file containing phase information was generated using rigid body refinement in REFMAC (Murshudov, G. N., Vagin, A. A., Lebedev, A., Wilson, K. S, and Dodson, E. J. Efficient anisotropic refinement of macromolecular structures using FFT. *Acta Crystallogr. D Biol. Crystallogr.* 55 (Pt 1), 247-255, January 1999) which was used for automated model building with arp/warp (Morris, R. J., Perrakis, A. and Lamzin, V. S. ARP/wARP and automatic interpretation of protein electron density maps. *Methods Enzymol.* 374, 229-244 (2003)). The resulting model was further modified manually using Xfit (McRee, D. E. XtalView/Xfit-A versatile program for manipulating atomic coordinates and electron density. J.

Struct. Biol. 125(2-3), 156-165, April 1999). Refinement was performed with CNS (Brunger, A. T., Adams, P. D., Clore, G. M., DeLano, W. L., Gros, P., Grosse-Kunstleve, R. W., Jiang, J. S., Kuszewski, J., Nilges, M., Pannu, N. S., Read, R. J., Rice, L. M., Simonson, T. and Warren, G. L. Crystallography and NMR system: A new software suite for macromolecular structure determination. *Acta Crystallogr. D Biol. Crystallogr.* 54 (Pt 5), 905-921, September 1998) and REFMAC (Murshudov, G. N. et al., 1999, see above).

4. Gel Filtration and Light Scattering

Gel filtration chromatography was carried out with the SMART system using a Superdex 75 PC 3.2/30 column (Pharmacia). Experiments were performed at room temperature in Buffer A (20 mM Tris-HCl pH 7.5, 100 mM NaCl, 1 mM DTT) at a flow rate of 0.04 ml/min. The molecular weight of the Mnk-2 KD was estimated using standard proteins (Bio-Rad). Multiangle-Laser-Light Scattering was done on a HR-10/30 Superdex-200 size exclusion column (Amersham) connected to a UV spectrometer and the Dawn and Optilab instruments XY (Wyatt Technology Corp.). A 30 µM solution of Mnk-2a was chromatographed in Buffer A and the UV absorption, the light scattering at 632.8 nm at 90 degree and the differential refraction of the elution profile were monitored and analyzed with the ASTRA software package (Wyatt, P. Light scattering and the absolute characterization of macromolecules. *Anal. Cim. Acta* 272, 1-40 (1993)).

Example 2

Figure 1B:
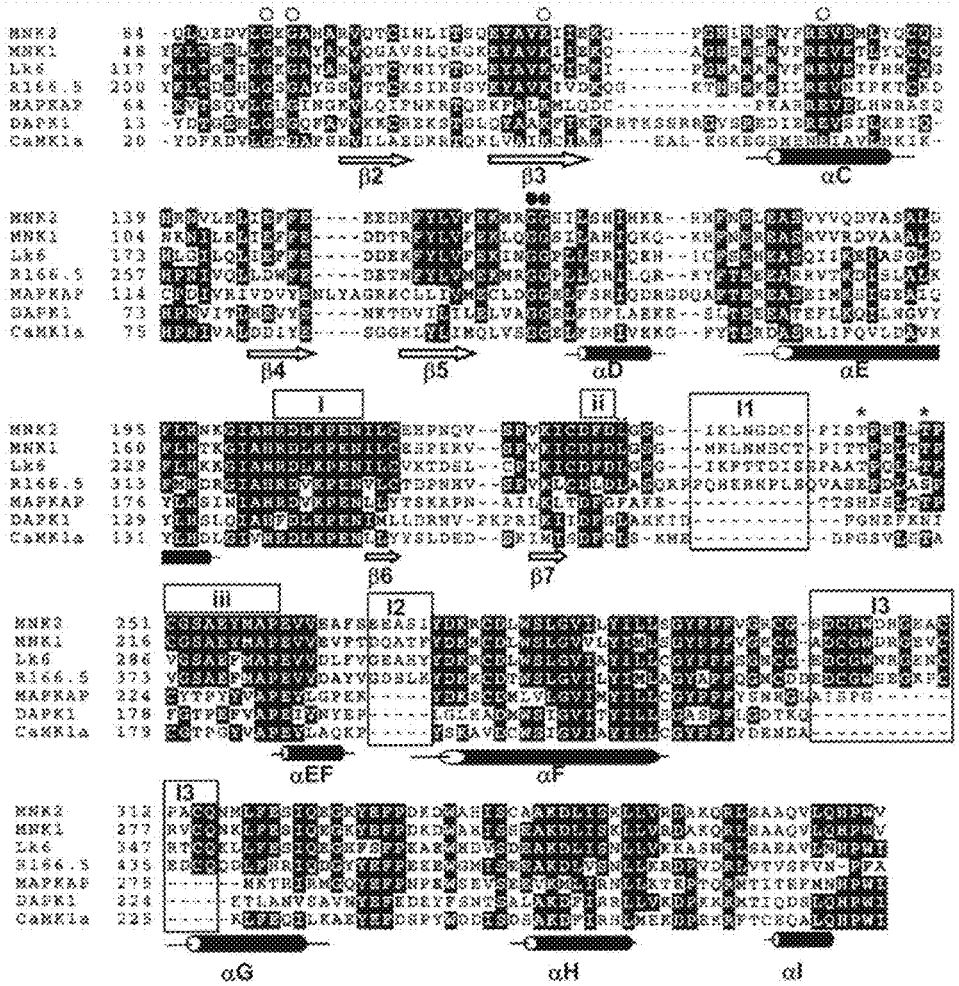
Figure 2D:
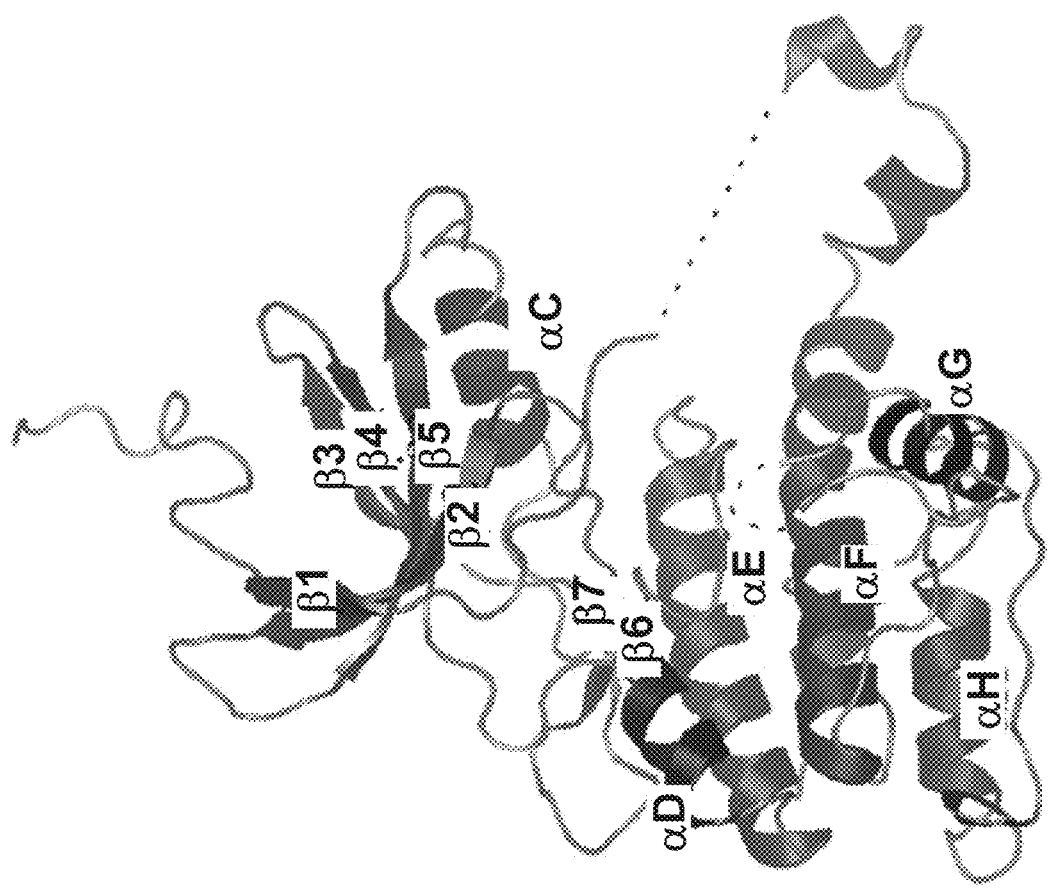

The p38-Diaryl Urea Inhibitor Co-Crystal Structures as Leads for Mnk-2-Specific Inhibitor Design The structure of protein kinase p38 is globally very similar to that of the Mnk-2 kinase domain (FIG. 1A). p38 features the typical DFG sequence motif in the ATP binding pocket. p38-directed inhibitors, based on a diaryl urea scaffold, have been designed, and co-crystal structures of p38 with two of these inhibitors (BMU and BIRB796, Pargellis et al. (2002), Nat. Struct. Biol. 9, 268-272) have been solved (PDB IDs 1KV1 and 1KV2, respectively). These inhibitors induce a non-canonical DFG conformation in p38 (denoted DFG-OUT), in which the phenylalanine is displaced from its standard position in a hydrophobic pocket (denoted DFG-IN), which it occupies in the apoenzyme and in other protein kinase structures (FIG. 1B). The DFG-OUT conformation of the DFG motif interferes with productive ATP binding by steric hindrance.

The Mnk-2 kinase region exhibits a DFD instead of a DFG motif (residues 226-228 of the sequence SEQ ID NO.: 19, see FIG. 1B). In the structure of the non-activated apoenzyme this DFD motif adopts a conformation similar to the non-canonical DFG-OUT conformation of p38 (FIG. 1B). Phe227 of Mnk-2 points into a cleft, which in p38 can be occupied by diaryl urea type inhibitors (FIG. 2A). The displacement is even more severe than in the p38-inhibitor complexes although no inhibitor was employed in the crystallization of the Mnk-2 kinase region (FIG. 1B). The DFD conformation seen in the Mnk-2 kinase region crystal structure is also incompatible with canonical ATP binding due to steric hindrance (FIG. 2B). This observation suggests that trapping of the DFD motif in the DFG/D-OUT conformation observed in the present crystal structure, would render Mnk-2 inactive, irrespective of the phosphorylation state.

It was explored whether a diaryl urea type inhibitor, BMU, could also bind to the Mnk-2 kinase region. After global superpositioning of the p38-BMU complex (PDB ID 1KV1) onto the Mnk-2 kinase region, slight manual adjustments in the BMU position and slight readjustments in some Mnk-2 side chain conformations, a Mnk-2-BMU complex model was obtained (FIGS. 2A and 2C). The inhibitor was seen to bind with its p-chloro-phenyl ring sandwiched between the aromatic rings of Phe227 and Phe159 of the sequence SEQ ID NO.: 19 (FIGS. 2A and 2C). Its tert-butyl moiety could be accommodated by a hydrophobic pocket in Mnk-2 (FIGS. 2A and 2C). The unusual Asp228 of the sequence SEQ ID NO.: 19 of Mnk-2 is remote from the BMU molecule in this model but could be targeted by additional chemical groups on modified inhibitors as demonstrated with other regions in p38 (compare the extended scaffold of BIRB796 in the 1KV2 structure with BMU in the 1KV1 structure of p38). In this fashion specificity for the DFD motif (the fingerprint of Mnk-2; instead of DFG in other kinases) may be achievable. Specific and strong binding to Mnk-2 could be supported by additionally modifying the p-chloro-phenyl and the tert-butyl groups of BMU to adapt novel inhibitors to the specific binding pockets of Mnk-2.

Example 3

Structure Determination and Overall Structure of Mnk-1-KR

Needlelike crystals of wild type Mnk1-KR (SEQ ID NO.: 18) were grown at 20° C. by vapor diffusion after mixing the protein solution with an equal volume of a reservoir solution containing 20% (w/v) PEG3350, 0.2M Ammonium sulfate and 0.1 M Na-Citrate, pH 5.4. Crystals were frozen (liquid nitrogen) in reservoir solution supplemented with 20% glycerol. Diffraction data were collected on beamline PXII (SLS, Villingen, Switzerland) at 100K on a MarResearch (Norderstedt, Germany) CCD detector and processed with the HKL package (Otwinowski and Minor, 1997). (see Table 3)

After molecular replacement using a truncated model of the Mnk-2-KR followed by density modification an interpretable electron density was obtained and the model could be refined to R/R$_{free}$ factors of 23.5/28.0% (Table 2). The asymmetric unit contains two Mnk-1-KR molecules which are related by a non-crystallographic two-fold axis. Molecule A exhibits lower temperature factors and a clearer electron density in several regions. The functionally important regions, however, are virtually identical between molecule A and molecule B. The final model spans the kinase domain of Mnk-1 and comprises residues 39-335 inclusive of the human Mnk-1 sequence according to SEQ ID NO.: 18. Mnk-1-KR preserves several global features of kinase architecture including the bilobal makeup. The N-terminal lobe bears the key elements necessary for ATP binding such as the Glycine rich loop and the Lys-Glu ion pair and is shaped of a five stranded twisted β-sheet and the regulatory helix αC (FIGS. 8A and 8B). The larger and predominantly α-helical C-terminal lobe contains the elements required for substrate binding and phosphate transfer, such as the catalytic loop (C-loop), the Magnesium binding loop (DFD motif) and the activation segment (FIGS. 8A and 8B). Two segments within the Mnk-1-KR exhibit strong conformational flexibility and can thus not be traced in the electron density: the core of the activation segment including the P+1 loop (residues 197-222 inclusive of the human Mnk-1 sequence according to SEQ ID NO.: 18) and the Mnk specific cysteine cluster including helix αG (residues 261-290 inclusive of the human Mnk-1 sequence according to SEQ ID NO.: 18).

The invention claimed is:

1. A crystalline human mitogen-activated kinase interacting kinase-1 (Mnk-1 kinase), wherein the crystal of said human Mnk-1 kinase has the space group $P4_32_12$ and unit cell dimensions of a=93.5 Å, b=93.5 Å, and c=175.2 Å, and wherein the human Mnk-1 kinase consists of residues 37 to 341 of SEQ ID NO: 18.

2. A method for producing a crystalline human mitogen-activated kinase interacting kinase-1 (Mnk-1 kinase), wherein the crystal of said human Mnk-1 kinase has the space group $P4_32_12$ and unit cell dimensions of a=93.5 Å, b=93.5 Å, and c=175.2 Å, and wherein the human Mnk-1 kinase consists of residues 37 to 341 of SEQ ID NO: 18, comprising the steps of:
 (i) expression of the human Mnk-1 kinase in cells,
 (ii) lysing the cells to recover a crude Mnk-1 kinase preparation,
 (iii) purifying the crude Mnk-1 kinase preparation, and
 (iv) crystallizing the purified human Mnk-1 kinase,
 wherein the step of crystallizing the purified human Mnk-1 kinase comprises the steps of:
 (i) obtaining a solution of the purified human Mnk-1 kinase of about 12 mg/ml in a buffer of 10 mM Tris/HCl (pH 7.5), 50 mM NaCl, 1 mM DTT; and
 (ii) crystallizing the purified human Mnk-1 kinase by the vapor diffusion at 20° C. by mixing the protein solution of (i) with a reservoir buffer of 20% (w/v) PEG3350, 0.2M ammonium sulfate and 0.1 M sodium citrate, pH 5.4.

3. The method according to claim 2, wherein the Mnk-1 kinase is expressed as a fusion protein in *E. coli*.

4. The method according to claim 2, wherein the Mnk-1 kinase is purified using a column binding to a fusion tag, wherein said fusion tag is attached to the Mnk-1 kinase.

* * * * *